United States Patent
Li et al.

(10) Patent No.: US 8,883,749 B2
(45) Date of Patent: Nov. 11, 2014

(54) TRANSCRIPTION FACTOR INHIBITORS AND RELATED COMPOSITIONS, FORMULATIONS AND METHODS

(75) Inventors: Pui-Kai Li, Galloway, OH (US); Chenglong Li, Dublin, OH (US); Jiayuh Lin, Dublin, OH (US)

(73) Assignees: The Ohio State University, Columbus, OH (US); Nationwide Children's Hospital, Inc., Columbus, OH (US)

( * ) Notice: Subject to any disclaimer, the term of this patent is extended or adjusted under 35 U.S.C. 154(b) by 853 days.

(21) Appl. No.: 12/954,038

(22) Filed: Nov. 24, 2010

(65) Prior Publication Data

US 2011/0212911 A1  Sep. 1, 2011

Related U.S. Application Data

(60) Provisional application No. 61/264,154, filed on Nov. 24, 2009.

(51) Int. Cl.
*A61K 31/704* (2006.01)
*A61K 31/7068* (2006.01)
*A61P 35/00* (2006.01)
*C07C 303/38* (2006.01)
*C12N 5/00* (2006.01)
*C07C 311/29* (2006.01)

(52) U.S. Cl.
CPC .................. *C07C 311/29* (2013.01)
USPC ............. 514/34; 435/29; 435/375; 435/6.14; 514/49; 514/602; 564/88

(58) Field of Classification Search
CPC .................................................... C07C 311/29
USPC ............... 514/34, 49, 602; 435/29, 375, 6.14; 564/88
See application file for complete search history.

(56) References Cited

U.S. PATENT DOCUMENTS

| | | | |
|---|---|---|---|
| 5,856,358 A | 1/1999 | Benetti et al. | |
| 5,864,048 A | 1/1999 | Di Napoli | |
| 2004/0052762 A1 | 3/2004 | Yu et al. | |
| 2009/0069420 A1 | 3/2009 | Turkson et al. | |
| 2009/0247495 A1 | 10/2009 | Xie et al. | |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994.*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Bhasin, D. et al., "Design, Synthesis, and Studies of Small Molecule STAT3 Inhibitors," Bioorganic & Medicinal Chemistry Letters, 2008, pp. 391-395, vol. 18.

(Continued)

*Primary Examiner* — Savitha Rao
(74) *Attorney, Agent, or Firm* — MacMillan, Sobanski & Todd, LLC

(57) ABSTRACT

The present invention provides small molecules useful to affect cancer cells, along with related methods. The present compounds, formulations, kits and methods are useful for a variety of research, diagnostic and therapeutic purposes. STAT3 inhibitors, particularly LLL12, are disclosed. The STAT3 inhibitors are useful to treat breast cancer in general and breast cancer initiating cells in particular.

39 Claims, 29 Drawing Sheets

(56) References Cited

OTHER PUBLICATIONS

Ehrlich, B.E. et al., "Paramecium Calcium Channels are Blocked by a Family of Calmodulin Antagonists," Proc. Natl. Acad. Sci. USA, Aug. 1988, pp. 5718-5722, vol. 85.

Lin, L. et al., "New Curcumin Analogues Exhibit Enhanced Growth-Suppressive Activity and Inhibit AKT and Signal Transducer and Activator of Transcription 3 Phosphorylation in Breast and Prostate Cancer Cells," Cancer Science, Sep. 2009, pp. 1719-1727, vol. 100, No. 9.

PCT International Search Report and the Written Opinion, PCT/US10/57757 filed Nov. 23, 2010, dated Mar. 14, 2011, [53-50801].

Song, H. et al., "A Low-Molecular-Weight Compound Discovered Through Virtual Database Screening Inhibits Stat3 Function in Breast Cancer Cells," PNAS, Mar. 2005, pp. 4700-4705, vol. 102, No. 13.

Turkson, J. et al., "Stat3 Activation by Src Induces Specific Gene Regulation and is Required for Cell Transformation," Molecular and Cellular Biology, May 1998, pp. 2545-2552, vol. 18, No. 5.

\* cited by examiner

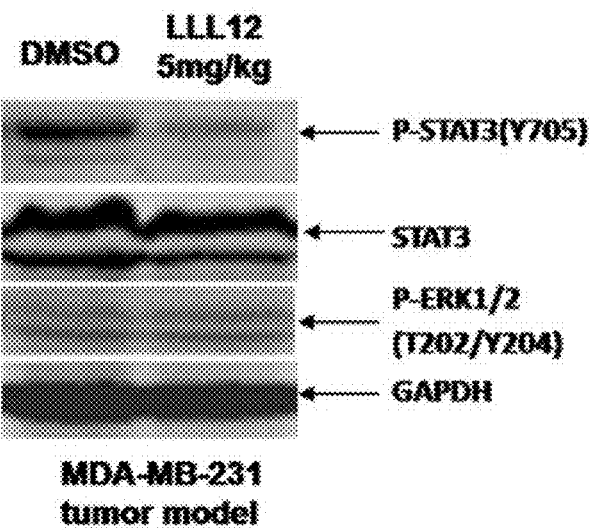
Figure 9C
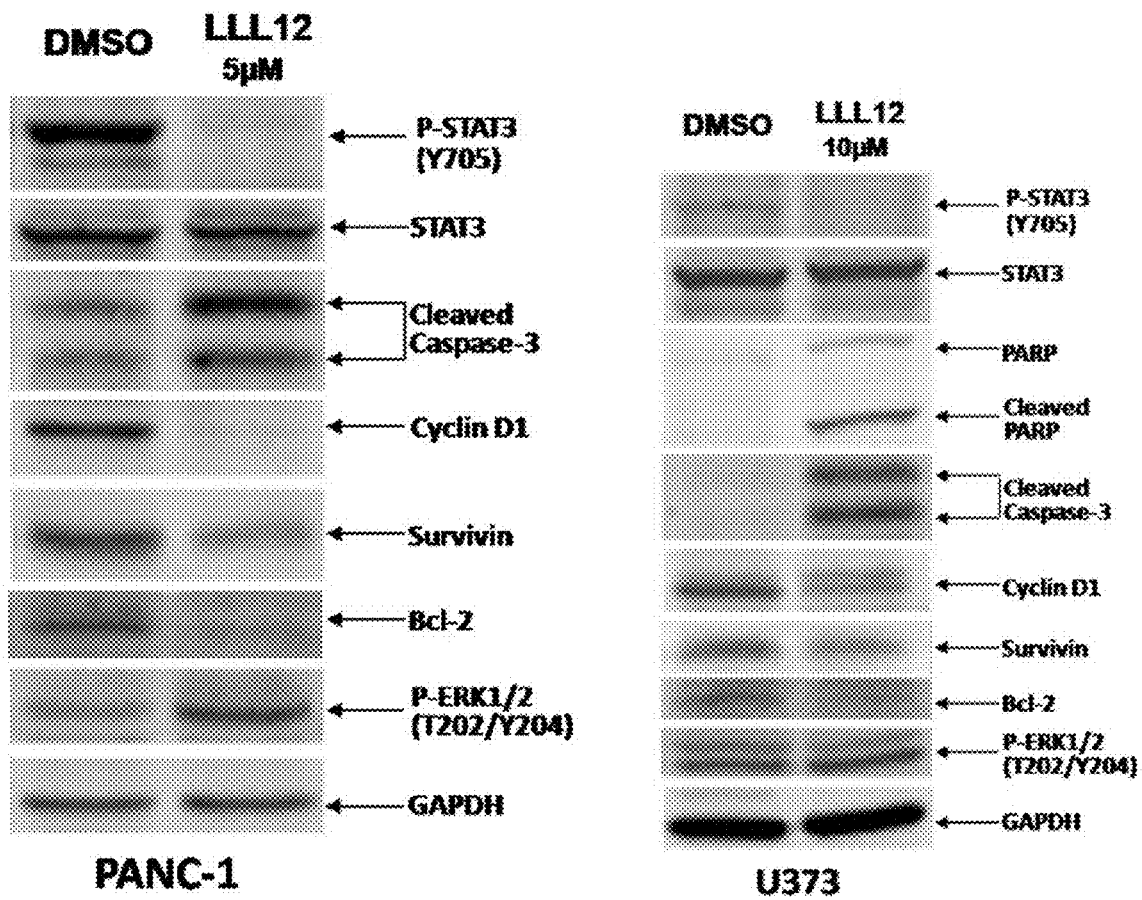
Figure 10A
Figure 10B

Figure 15B
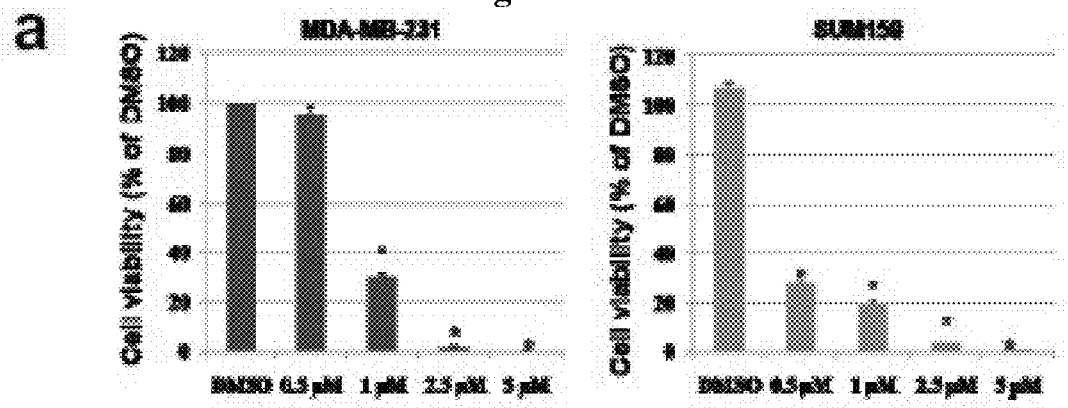
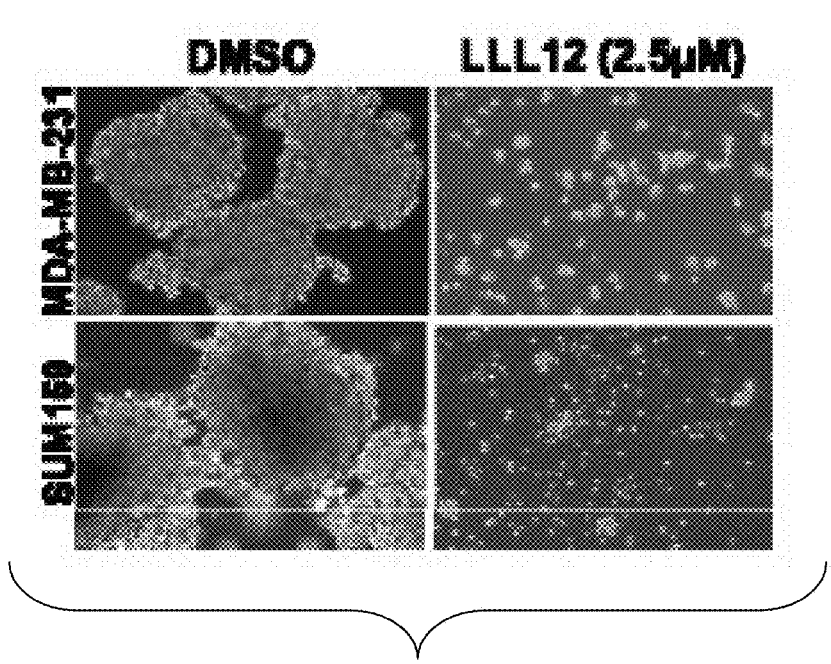
Figure 15C

TRANSCRIPTION FACTOR INHIBITORS AND RELATED COMPOSITIONS, FORMULATIONS AND METHODS

CROSS-REFERENCE TO RELATED APPLICATIONS

This application claims the benefit of U.S. Provisional Application No. 61/264,154 filed Nov. 24, 2009, the disclosure of which is incorporated herein by reference.

STATEMENT REGARDING FEDERALLY SPONSORED RESEARCH

This invention was made with Government support under grant R21CA133652-01 awarded by the National Institutes for Health (NIHR21). The government has certain rights in the invention.

TECHNICAL FIELD OF THE INVENTION

The present invention is based, in part, on the discovery of a new class of small molecules that inhibit STAT3 activation. Inhibition of STAT3 activation affects cancer-related transcription factors, which in turn increases apoptosis of cancer cells. Other cellular function effects related to administration of these new STAT3 activation inhibitors have also been shown.

REFERENCE TO SEQUENCE LISTING SUBMITTED VIA EFS-WEB

This application is being filed electronically via the USPTO EFS-WEB server, as authorized and set forth in MPEP§1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 604_50802_SEQLIST_OSU-00902.txt, created on Nov. 22, 2010 and is 5,753 bytes in size.

BACKGROUND OF THE INVENTION

Cancer is the second leading cause of death in the United States, with the various forms being attributed to one in four deaths. Approximately one in two men and one in three women will be diagnosed with an invasive cancer in their lifetime. Breast cancer is the leading type of cancer affecting women. It is estimated that breast cancer accounts for just over a quarter of all newly diagnosed cancer cases in women. Pancreatic cancer is the fourth leading cause of cancer deaths in the United States. Diagnosis is followed by a poor prognosis, with a five-year survival rate of only 5%. Worldwide, the survival rate for pancreatic cancer is only 1%. Gliomas, a type of brain cancer, account for more than 75% of all primary malignant brain tumors. The most common type of glioma, glioblastoma, is also the most severe. It is a highly aggressive cancer and continues to have a pool survival rate, with most cases becoming fatal within two years of diagnosis. The large number of cases and poor survival rates under current therapies necessitate the search for novel target therapies for cancer.

The Signal Transducers and Activators of Transcription (STAT) proteins are transcription factors that participate in cancer proliferation. STATs have been shown to relay signals from cytokines and growth factors. Constitutive activation of STATs has been found to contribute to oncogenesis. STAT3 in particular, is constitutively active in a wide variety of human malignancies; including breast and pancreatic cancer and glioblastoma. STAT3 is considered to be an oncogene due to its ability to promote malignancy. Experiments have shown that constitutively active STAT3 is sufficient for inducing cellular transformation. Further research shows a resistance to transformation in STAT3 deficient fibroblasts. Constitutively active STAT3 has also been shown to have the potential to alter the phenotype of non-malignant cells into malignant-like cells.

Persistent activation of STAT3 has been implicated in both the induction of cancer and processes promoting the survival of cancer. STAT3 activation occurs when the Tyrosine 705 ($Tyr_{705}$) residue is phosphorylated, leading to dimerization and translocation from the cytoplasm to the nucleus. In the nucleus, STAT3 binding to target genes induces the transcription and up regulation of proliferation and anti-apoptotic associated proteins. Therefore, constitutive STAT3 signaling is involved in stimulating cell cycle progression and preventing apoptosis which both contribute to malignant progression. STAT3 has also been found to promote angiogenesis. In addition, persistently activated STAT3 plays a role in impairing both innate and adaptive immune responses by enhancing immunologic tolerance and enabling cancer cells to evade immune surveillance. Further, the survival of these tumors appears to depend on the presence of STAT3 signaling.

The implications of constitutive STAT3 signaling in tumors have presented it as a possible target for cancer treatment. Experiments aimed at blocking STAT3 signaling using dominant-negative STAT3, RNA interference, and STAT3 antisense oligonucleotides have been attempted. It was also determined that in normal cells, blocking STAT3 is neither harmful nor toxic to the cells. Given the oncogenic functions of STAT3, directly targeting STAT3 signaling represents a potential therapeutic approach to treating cancer.

The inventors herein have now shown, inter alia, that a new class of small molecules inhibits STAT3, resulting in apoptosis of cancer cells.

This invention therefore contributes effective therapeutic, diagnostic and prophylactic agents having increased positive results and fewer side effects. The invention also provides methods for making related compounds, formulations, compositions, kits, etc.

SUMMARY OF THE INVENTION

In a first broad aspect, there are provided compounds having the general Formula I:

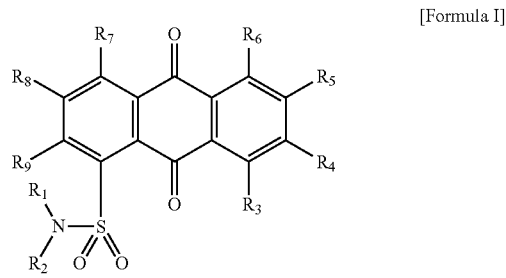

[Formula I]

wherein
R$_1$, and R$_2$ are independently hydrogen or alkyl$_M$, wherein M is 1, 2, 3, 4, 5 or 6 carbons;

$R_3$, $R_5$, $R_6$, $R_8$, and $R_9$ are independently hydrogen, alkyl, alkoxy, halogen, $NO_2$, $NH_2$, or hydroxyl;

$R_4$ and $R_7$ are independently alkyl, alkoxy, O-alkyl, N-alkyl, aromatic, heteroaromatic, cyclic, or heterocyclic.

Preferred are those compounds as described wherein $R_1$, $R_2$, $R_3$, $R_4$, $R_5$, $R_7$, $R_8$ and $R_9$ are each hydrogen and $R_6$ is hydroxyl. Also provided are compositions of matter, comprising a compound herein and a pharmaceutically-acceptable excipient, carrier, diluent or salt. Prodrugs, intermediates, racemates and metabolites related to the present compounds are also provided.

For instance, the compound of the Formula II is provided, as are compositions of matter comprising a compound of Formula II and a pharmaceutically-acceptable excipient, carrier, diluent or salt. Prodrugs, intermediates, racemates and metabolites related to the present compounds are also provided.

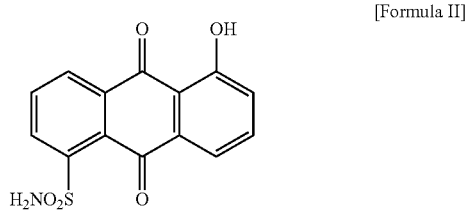 [SMILES: NS(=O)(=O)c1cccc2c1C(=O)c1cccc(O)c1C2=O]

[Formula II]

In another there is provided herein a method to synthesize a compound of Formula I which includes: reacting an unsubstituted or substituted naphthalene sulfonyl chloride compound with a nitrogen containing compound to form an unsubstituted or substituted naphthalene sulfonyl amine; oxidizing the unsubstituted or substituted naphthalene sulfonyl amine of step i) to yield an unsubstituted or substituted naphthoquinone compound; and, catalyzing via a Diels-Alder reaction of 3-hydroxy-2-pyrone with the unsubstituted or substituted naphthoquinone compound of step ii) to yield a compound of formula I.

In certain embodiments, the nitrogen containing compound of step i) comprises ammonium hydroxide and the naphthalene sulfonyl chloride is unsubstituted.

In another aspect of the present invention, there are provided methods to inhibit STAT3 activation in a cell, comprising introducing a compound of Formula I herein to a STAT3-expressing cell, and measuring STAT3 activation inhibition. Preferred are those methods wherein inhibition is measured by observing a STAT3-related effect, such as: cell apoptosis; prevention of STAT3 SH2 dimerization; a decrease in the levels of expression of STAT3 phosphorylation; inhibition of downstream targets of STAT3, especially cyclin; Bcl-2; and surviving and/or induction of cleaved PARP and caspase-3; a reduction in STAT3 phosphorylation after inducing IL-6 in MDA-MD-453 breast cancer cells; reduction of STAT3 DNA binding activity after compound introduction; reduction of STAT3-dependent transcriptional activity after compound introduction.

In another aspect of the present invention, there are provided methods to inhibit transcription of STAT3 regulated genes, comprising administering a compound of Formula I herein. Preferred are those methods wherein said transcription inhibition is measured by reverse transcriptase PCR.

In another aspect of the present invention, there are provided methods to decrease the ability of tumor cells to form colonies, comprising a administering a compound of Formula I herein to a tumor cell-containing medium. Preferred are those methods wherein the tumor cell-containing medium is a mammalian cell culture, although those methods wherein said tumor cell-containing medium is a mammal are also preferred. More preferred methods are those wherein said mammal is selected from the group consisting essentially of: human; livestock; companion animal; and zoo animal.

In another aspect of the present invention, there are provided methods to inhibit tumor cell migration, comprising administering a compound of Formula I herein to a tumor cell-containing medium. Preferred are those methods wherein the tumor cell-containing medium is a mammalian cell culture, although those methods wherein said tumor cell-containing medium is a mammal are also preferred. More preferred methods are those wherein said mammal is selected from the group consisting essentially of: human; livestock; companion animal; and zoo animal.

In another aspect of the present invention, there are provided methods to inhibit tumor cell proliferation, comprising administering a compound of Formula I herein to a tumor cell-containing medium. Preferred are those methods wherein the tumor cell-containing medium is a mammalian cell culture, although those methods wherein said tumor cell-containing medium is a mammal are also preferred. More preferred methods are those wherein said mammal is selected from the group consisting essentially of: human; livestock; companion animal; and zoo animal.

In another aspect of the present invention, there are provided methods to treat cancer in a patient in need of such treatment, comprising administering a pharmaceutically-acceptable formulation of at least one compound of Formula I herein. Preferred are those methods wherein the cancer treated is selected from the group consisting essentially of: breast cancer; glioblastoma; and pancreatic cancer. More preferred are those methods which further comprises administering to the patient at least one additional chemotherapeutic drug. Most preferred are those methods wherein said additional chemotherapeutic drug is doxorubicin, gemcitabine or a combination of the two.

Also provided by the present invention are methods to determine the presence of tumor cells in a sample, comprising introducing a compound of Formula I to a cell sample, and measuring STAT3 inhibition.

Also provided are methods to identify compounds useful to inhibit STAT3 activation, comprising comparing the ability of a compound of Formula I to inhibit STAT3 activation to the ability of a test compound to inhibit STAT3 activation.

Also provided are kits comprising a compound of Formula I. Those kits which comprise a compound of Formula I and also comprise nucleic acid molecules useful to identify STAT3 transcription are preferred.

DEFINITIONS

"Observing" means ascertaining physical (including chemical, biological, crystallographical) attributes, via scientifically-reliable assay, including optional use of any scientifically-reliable assay(s) described herein, and optional use of computer generation and/or analysis of the results of any assay(s).

All other terms herein have the meaning as understood in the global scientific art (in the case of a scientific term) and/or in general U.S. English usage (in the case of non-scientific terms).

BRIEF DESCRIPTION OF THE FIGURES

(FIG. 1A) Synthesis of LLL12 (includes chemical structure). (FIG. 1B) Computer model of LLL12 binds to STAT3 SH2 domain. The ball-and-stick model of pTyr$_{705}$-Leu$_{706}$ is the binding mode of the partnering SH2 during the STAT3 homodimerization. LLL12 effectively displaces its binding through stronger binding to pTyr705 binding site, indicating LLL12 can efficiently prevent STAT3 SH2 dimerization.

(FIG. 5A) STAT3-dependent transcriptional activity was analyzed in a luciferase assay. MDA-MB-231 breast cancer cloned cells that stably integrate the STAT3-dependent luciferase reporter construct, pLucTKS3 were used. Results are reported relative to a pLucTKS3-transfected sample treated with DMSO set at 100%. Statistical significance (P<0.05) relative to DMSO is designated by an asterisk. (FIG. 5B) Transcription of STAT3-regulated genes is inhibited by LLL12. Reverse transcriptase PCR reveals decreased expression of STAT3 target genes over a DMSO control following treatment with LLL12.

(FIG. 6A) Colony formation of MDA-MB-231 cells in soft agar is inhibited by LLL12. The potency of LLL12 was assessed further in an anchorage independent environment through a colony formation assay. Treatment with LLL12 greatly decreased the ability of MDA-MB-231 cells to form colonies in comparison to a DMSO control. (FIG. 6B) LLL12 inhibits cell migration in MDA-MB-231 breast cancer cells. A wound healing assay reveals that LLL12 has a significant impact on MDA-MB-231 cell migration. The ability of the cells to migrate is increasingly inhibited by an increase in dose of LLL12. Statistical significance (P<0.05) relative to the DMSO control is designated by an asterisk. (FIG. 6C) A cell viability assay (MTT) was done to determine if the effect of LLL12 on MDA-MB-231 cell migration was due to its ability to inhibit cell proliferation. The time points of treatment (4 hours with LLL12) and incubation (additional 20 hours without LLL12) used in the wound healing assay was applied in the viability assay. The ability of LLL12 to inhibit cell migration does not appear to be due to an inhibition of cell proliferation.

(FIG. 7A) MDA-MB-231 breast cancer cells were treated with LLL12 and doxorubicin individual and in combination. (FIG. 7B) HPAC pancreatic cancer cells were treated with LLL12 and gemcitabine individual and in combination. Cell viability was determined by MTT assay. A synergistic effect between LLL12 and doxorubicin or gemcitabine is indicated by an asterisk.

(FIG. 8A) LLL12 induced capase-3 cleavage was rescued in U87 cells when STAT3-C protein was expressed. (FIG. 8B) The inhibition of cell viability of LLL12 in U87 cells was also reduced in the presence of STAT3-C protein in MTT assay (*P<0.05).

FIGS. 9A-9C. Effect of LLL12 on tumor growth in mouse xenografts with MDA-MB-231 breast cancer cells (FIG. 9A) or U87 glioblastoma cells (FIG. 9B). After the tumor development, the mice were given daily intraperitoneal dosages of 2.5-5 mg/kg LLL12 or DMSO (*P<0.05). STAT3 but not ERK1/2 phosphorylation of MDA-MB-231 tumor tissue samples from these mice were also decreased (FIG. 9C).

FIGS. 10A-10B. LLL12 inhibits STAT3 phosphorylation, down-regulates STAT3 downstream target genes (cyclin D1, survivin and Bcl-2) expression and induces apoptosis in (FIG. 10A) PANC-1 pancreatic cancer cells and (FIG. 10B) U373 glioblastoma cells.

(FIG. 11A) Representative flow cytometry analysis of ALDH enzymatic activity in SUM159 breast cancer cells was shown. (FIG. 11B) ALDH$^+$ and ALDH$^-$ subpopulations were separated from MDA-MB-231, SUM159, and SK-BR-3 breast cancer cells by flow cytometry. Phosphorylation of STAT3 (Y705), and ERK 1/2 (T202/Y204), was detected by Western blot;

(FIG. 12A) LLL12 inhibits STAT3 phosphorylation and induces apoptosis in ALDH$^+$ breast cancer initiating cells. ALDH$^+$ breast cancer initiating cells were treated with 5 µM of LLL12 or DMSO. (FIG. 12B) Inhibition of the expression of STAT3 downstream target genes in ALDH$^+$ subpopulation of breast cancer cells by LLL12. (FIG. 12C) STAT3 ShRNA inhibits STAT3 phosphorylation and induces cleaved caspase-3 in the absence or presence of LLL12.

FIGS. 15A-15D. STAT3 phosphorylation of the ALDH$^+$/CD44$^+$/CD24$^-$ subpopulation of breast cancer cells is higher than un-separated and the ALDH$^-$/CD44$^+$/CD24$^+$ subpopulations. (FIG. 15A) ALDH$^+$/CD44$^+$/CD24$-$ and ALDH$^-$/CD44$^+$/CD24$^+$ subpopulations were separated from MDA-MB-231 and SUM159 breast cancer cells by flow cytometry. Phosphorylation of STAT3 (Y705), and ERK 1/2 (T202/Y204), was detected by Western blot. (FIG. 15A-B) LLL12 inhibits STAT3 phosphorylation and induces apoptosis in ALDH$^+$/CD44$^+$/CD24$^-$ breast cancer initiating cells. ALDH$^+$/CD44$^+$/CD24$-$ breast cancer initiating cells were treated with 5 μM of LLL12 or DMSO. (FIG. 15A-C) Inhibition of the expression of STAT3 downstream target genes in ALDH$^+$/CD44$^+$/CD24$^-$ subpopulation of breast cancer cells by LLL12. (FIG. 15A-D) Tumorsphere development was observed under the microscope 10 to 15 days later. (FIG. 15A) LLL12 suppressed tumor growth in mouse xenografts with SUM-159 breast cancer initiating cells (ALDH$^+$/CD44$^+$/CD24$^-$ cells). Reduction of tumor volume in all six LLL12-treated mice compared to DMSO vehicle group (*P<0.05).

DETAILED DESCRIPTION

Figure 1A:
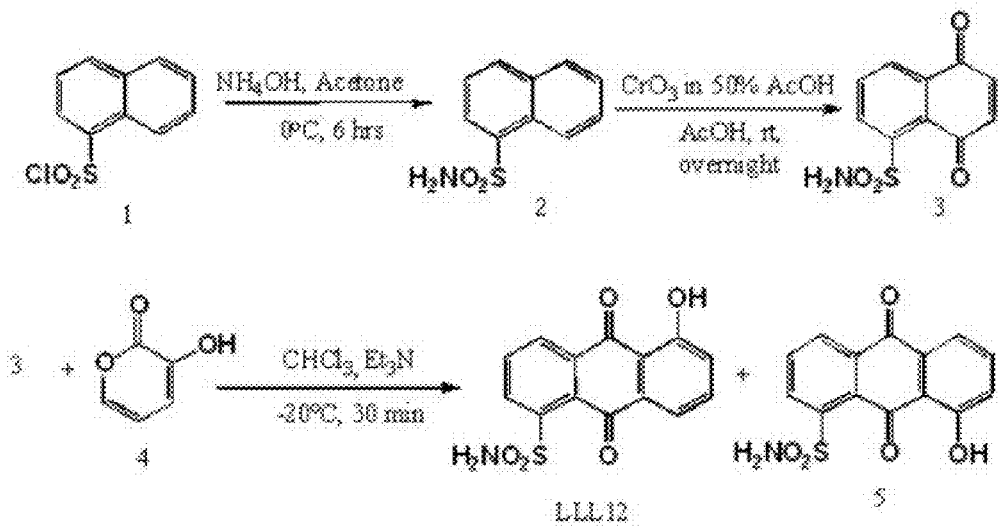
FIGS. 1A-1B.

The present invention provides non-peptide, cell-permeable, small molecules which target STAT3. These molecules are newly discovered to inhibit STAT3 phosphorylation (Tyr705) and induce apoptosis (as indicated by the increases of cleaved caspase-3 and poly-ADP ribose polymerase or "PARP") in various human breast, pancreatic and glioblastoma cancer cell lines expressing elevated levels of STAT3 phosphorylation. These molecules also inhibit STAT3 phosphorylation induced by Interleukin-6 in MDA-MB-453 breast cancer cells. The inhibition of STAT3 signaling by the present molecules was confirmed by the inhibition of STAT3 DNA binding activity and STAT3-dependent transcriptional luciferase activity. Downstream targets of STAT3, cyclin D1, Bcl-2, and survivin were also down-regulated, at both protein and mRNA level. The present molecules are potent inhibitors of cell viability, with $IC_{50}$ values ranging between 0.16 μM and 3.09 μM, which are lower than reported JAK2 inhibitor WP1066 and STAT3 SH2 inhibitor S3I-201 in six cancer cell lines expressing elevated levels of STAT3 phosphorylation. In addition, these molecules inhibit colony formation, cell migration and work synergistically with doxorubicin and gemcitabine. Furthermore, these molecules demonstrate a potent inhibitory activity on breast and glioblastoma tumor growth in mouse xenograft model. This discovery indicates that these molecules are useful as therapeutic agents for breast and pancreatic cancer cells as well as glioblastoma cells expressing constitutive STAT3 signaling.

LLL12 is a Novel Small Molecule that Targets STAT3.

The phosphoryl tyrosine 705 (pY705) is critical for the biological function of STAT3, as it is critical for dimerization. The phosphoryl tyrosine 705 is located on a loop segment of the SH2 domain and binds together with several adjacent amino acid residues (leucine 706, threonine 708, and phenylalanine 710) to a cavity on the SH2 domain of the other STAT3 monomer. The inventors designed a compound, LLL12, which binds to STAT3 SH2 domain. The structure and synthesis of LLL12 was shown in FIG. 1A. To optimize potency and selectivity, the main scaffold of LLL12 contains fragments that directly contact the pY705 binding site of STAT3 (FIG. 1B). A simulated docking model shows that the sulfonamide tail of LLL12 occupy the pY705 binding pocket of STAT3 with at least three hydrogen bonds. Simulated binding energy (−7.8 Kcal/mol) of LLL12 to STAT3 predicts that it will be a potent inhibitor of the constitutive STAT3 pathway.

LLL12 Inhibits STAT3 Phosphorylation and Induces Apoptosis in Human Breast and Pancreatic Cancer Cells and Glioblastoma Cells.

LLL12 was evaluated for its effect on breast cancer cells (MDA-MB-231 and SK-BR-3), pancreatic cancer cells (HPAC and PANC-1), and glioblastoma cells (U87 and U373) which express elevated levels of STAT3 phosphorylation. LLL12 inhibited STAT3 phosphorylation at tyrosine residue 705 (Tyr 705) in all six cancer cell lines (FIGS. 2A-D). LLL12 was not found to inhibit phosphorylation of other kinase, such as ERK1/2, mTOR, and Src, indicating selectivity for STAT3. As shown in FIGS. 2A-D, downstream targets of STAT3, such as cyclin D1, survivin, and Bcl-2, were down regulated by LLL12. The inhibition of STAT3 phosphorylation by LLL12 seems to be consistent with the induction of apoptosis as evidence by the cleavages of PARP and caspase-3 (FIGS. 2A-D). The effect of LLL12 was also examined in cells which do not express elevated levels of STAT3 phosphorylation [human Pancreatic Duct Epithelial (HPDE) cells, human Mammary Epithelial cells (HMEC), human hepatocytes (HH), and WI-38 normal lung fibroblasts]. LLL12 did not induce cleaved PARP or caspase-3 in any of these cells lines (FIG. 2E). This indicates that LLL12 is selective for cancer cells expressing elevated levels of STAT3 phosphorylation.

LLL12 Inhibits STAT3 Phosphorylation Induced by IL-6.

Figure 3:
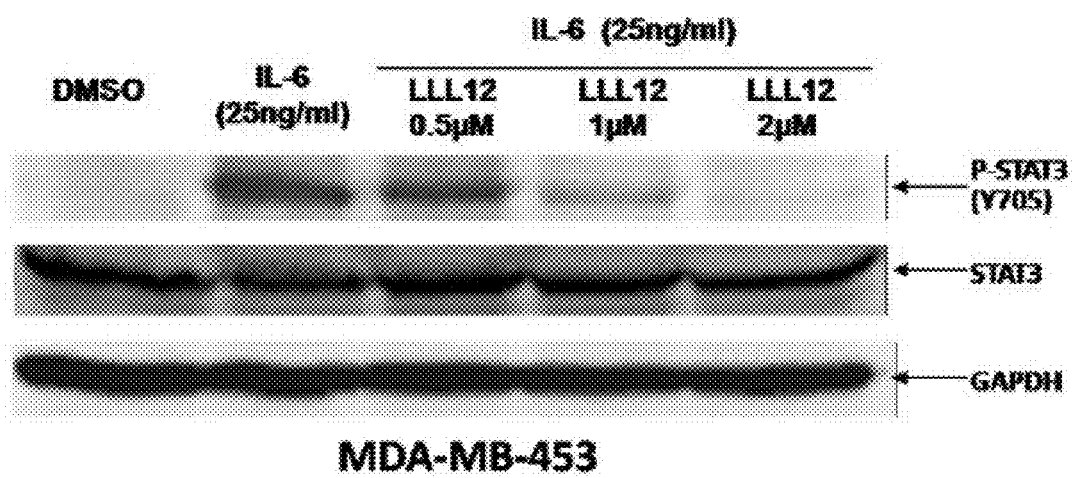
FIG. 3. LLL12 inhibits STAT3 phosphorylation induced by IL-6 in MDA-MB-453 breast cancer cells without STAT3 phosphorylation. The cells were serum starved overnight, then left untreated or were treated with LLL12 (0.5 µM-2 µM) or DMSO. After 2 hours the untreated and LLL12 treated cells were stimulated by IL-6 (25 ng/mL). The cells were harvested at 30 min and analyzed by western blot.

Activation of STAT3 can be induced by IL-6. MDA-MB-453 breast cancer cells, which do not express persistently phosphorylated STAT3, were used to determine if LLL12 is capable of inhibiting IL-6 induced STAT3 phosphorylation. The inventors found that IL-6 stimulates STAT3 phosphorylation in MDA-MB-453 cells. This stimulation of STAT3 phosphorylation was blocked by LLL12 in a dose-dependent manner (FIG. 3). These results support that LLL12 is a potent inhibitor of STAT3 phosphorylation in cancer cells.

LLL12 Inhibits STAT3 DNA Binding.

Figure 4A:
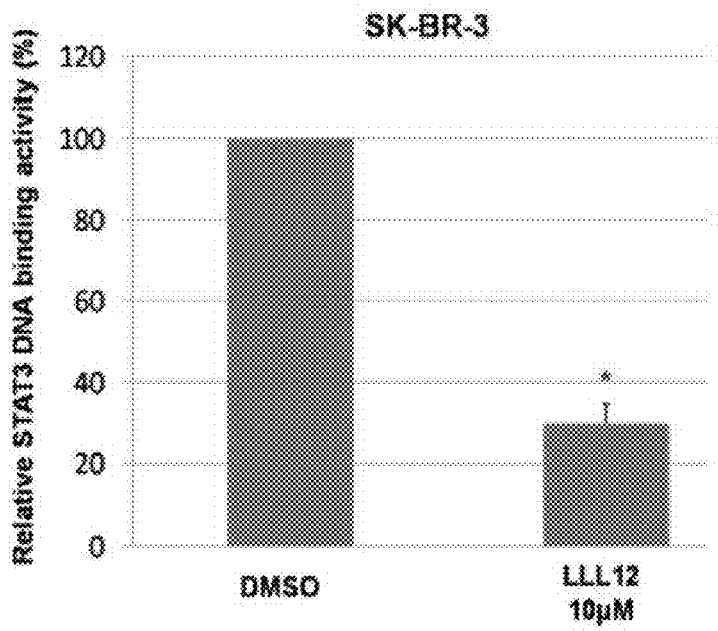
FIGS. 4A-4D. LLL12 has an inhibitory effect on STAT3 DNA binding activity and STAT3 dependent transcriptional activity. The nuclear extracts of (FIG. 4A) SK-BR-3, (FIG. 4B) MDA-MB-231, (FIG. 4C) HPAC, and (FIG. 4D) U87 cancer cells were analyzed for STAT3 DNA binding. STAT1 DNA binding was also looked at to demonstrate the specificity of LLL12 to STAT3 over STAT1 protein in (FIG. 4B) MDA-MB-231 and (FIG. 4D) U87 cancer cells. Statistical significance (P<0.05) relative to the DMSO vehicle control is designated by an asterisk.
Figure 4B:
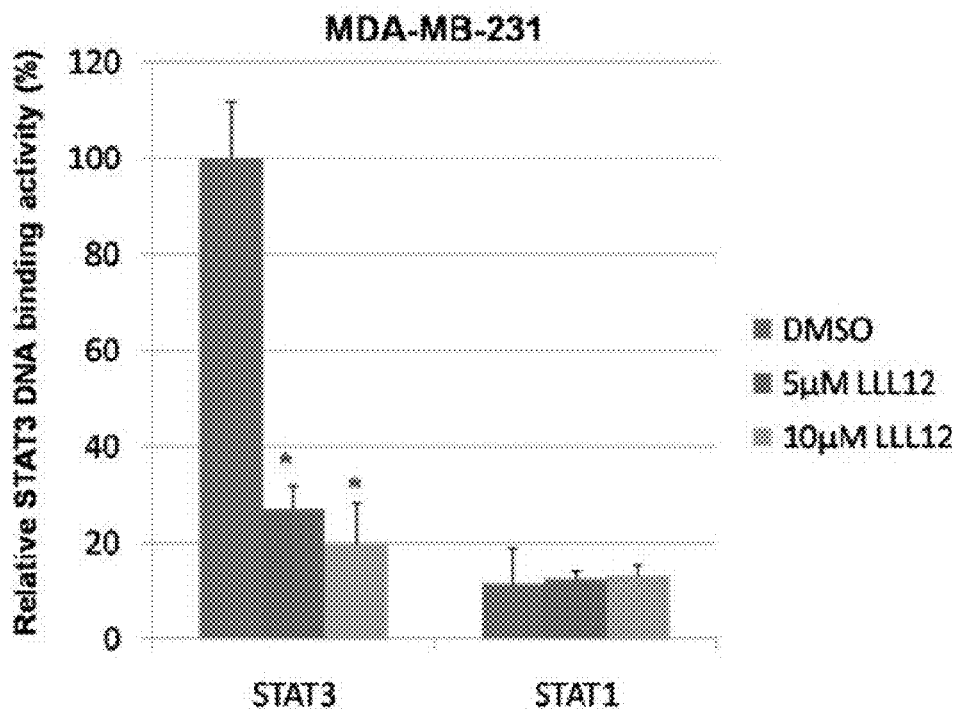
Figure 4C:
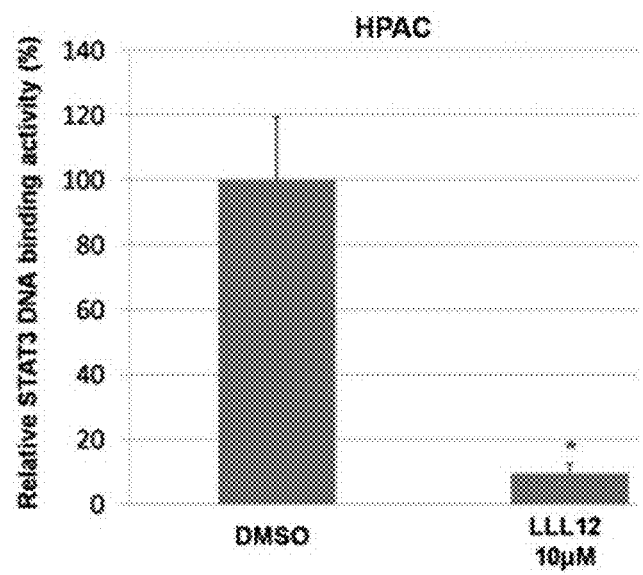

To confirm the inhibition of STAT3 signaling by LLL12, the inventors examined the inhibition of STAT3 DNA binding activity. LLL12 caused a statistically significant inhibition of STAT3 DNA binding activity in breast cancer cell lines, SK-BR-3 (FIG. 4A) and MDA-MB-231 (FIG. 4B), pancreatic cancer cell line, HPAC (FIG. 4C), and glioblastoma cell line, U87 (FIG. 4D) LLL12 did not inhibit STAT1 DNA binding activity (FIGS. 4B and 4D), indicating a specificity of LLL12 for STAT3 over STAT1

LLL12 Inhibits STAT3-Dependent Transcriptional Activities and Transcription of Downstream Targets of STAT3.

Figure 5A:
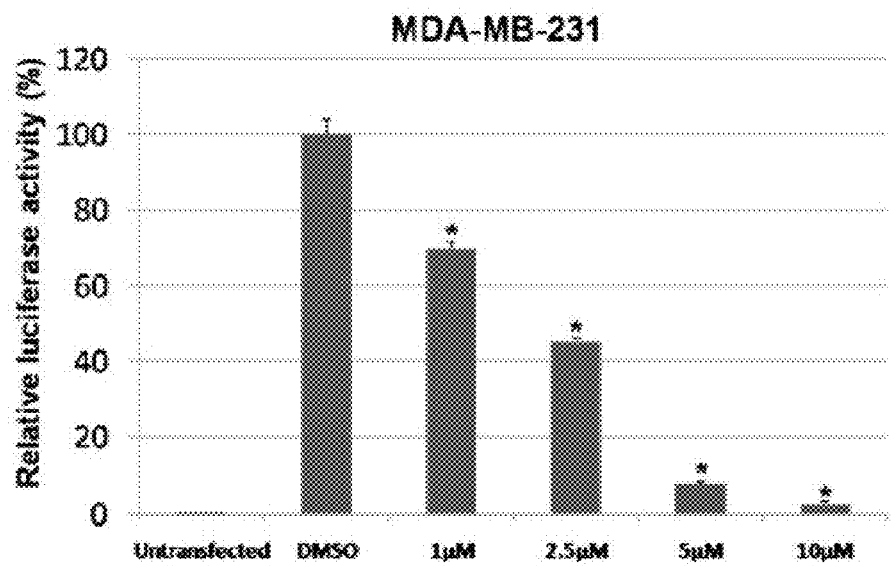
FIGS. 5A-5B.
Figure 5B:
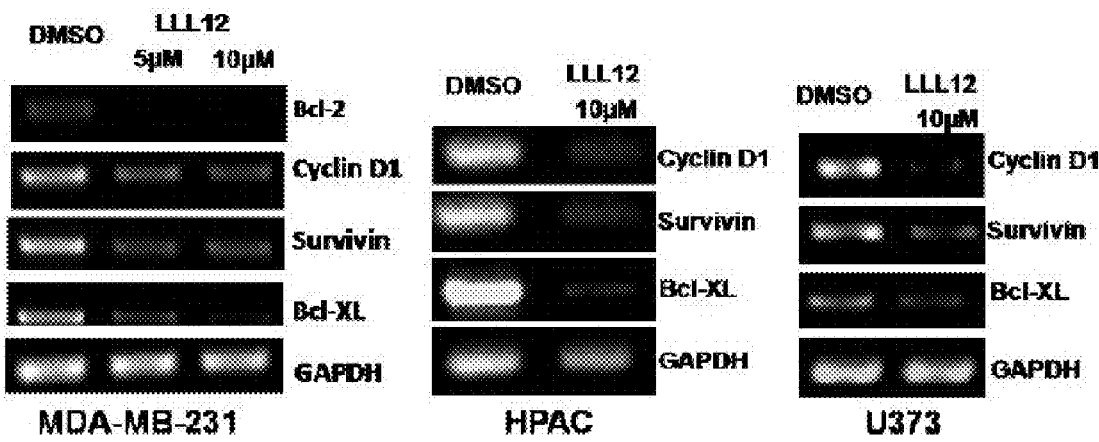

As mentioned above, STAT3 binding to the promoters of the target genes and induces the transcription of several proliferation and anti-apoptotic associated proteins. STAT3-dependent transcriptional luciferase activity was then examined after treated with LLL12 for 24 hours. As seen in the luciferase assay (FIG. 5A), LLL12 also inhibited STAT3-dependent transcriptional activity in a dose-dependent manner. To further analyze the impact of LLL12 on the inhibition of STAT3 the inventors looked at the transcription of downstream target genes of STAT3 by reverse transcriptase PCR. The inventors treated MDA-MB-231 breast cancer cells, HPAC pancreatic cancer cells and U373 gliobalstoma cells with LLL12 (5 or 10 µM) or DMSO for 24 h. Reverse Transcriptase PCR was run for cyclin D1, survivin, and Bcl-XL. The inventors found that treatment with LLL12 resulted in an inhibition of the transcription of STAT3-regulated genes (FIG. 5B).

Inhibition of Cell Proliferation/Viability in Human Breast and Pancreatic Cancer Cells and Glioblastoma Cells by LLL12.

STAT3 activation is important for cell proliferation and survival. Cell viability Assays were run to examine the inhibitory affect of LLL12 on human breast and pancreatic cancer cells and glioblastoma cells. A dose-dependent inhibition in tumor cell proliferation/viability was seen after 72 h of treatment. IC50 values were calculated for LLL12 and other previously characterized inhibitors (Table 2, Example 7); WP1066, a JAK2/STAT3 inhibitor, and S3I-201, STAT3 inhibitor. The inhibitory efficacy of the three compounds was compared. LLL12 is substantially more potent in the inhibition of cell viability than the other available inhibitors in all the cell lines analyzed.

Anchorage Independence and Cell Viability.

Figure 6A:
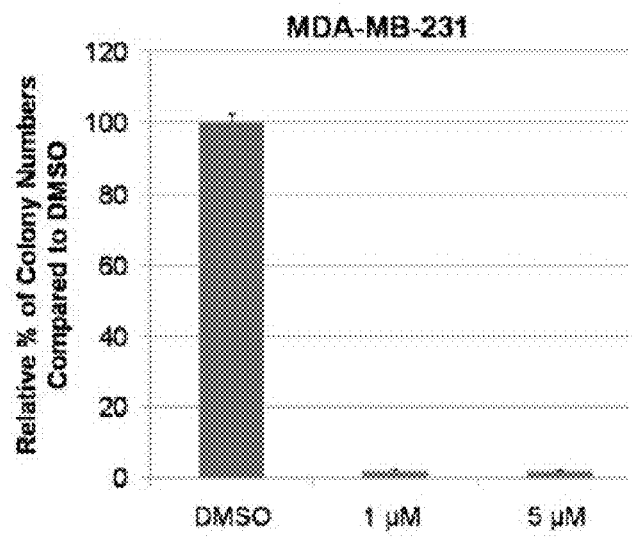
FIGS. 6A-6C.

An indicator of transformation is the ability of cells to grow in the absence of substratum attachment. Anchorage independent growth is vitally important in the formation of the tumor. The soft agar colony formation assay provides an assessment of tumor cells susceptibility to a drug in an anchorage independent environment. It is considered a more sensitive measure of toxicity, reflecting the efficacy of a drug, because it is analyzed when cells are in a proliferative state. The inventors examined the effect LLL12's ability to inhibit STAT3 would have on colony formation of MDA-MB-231 cells in soft agar. Compared to the DMSO control, treatment with LLL12 led to a decrease of over 95% in colony formation (FIG. 6A). The results of this assay further confirm what was seen in the MTT assay, LLL12 is a potent inhibitor for cancer cell viability.

LLL12 Inhibits Cell Migration in MDA-MB-231 Breast Cancer Cells.

Figure 6B:
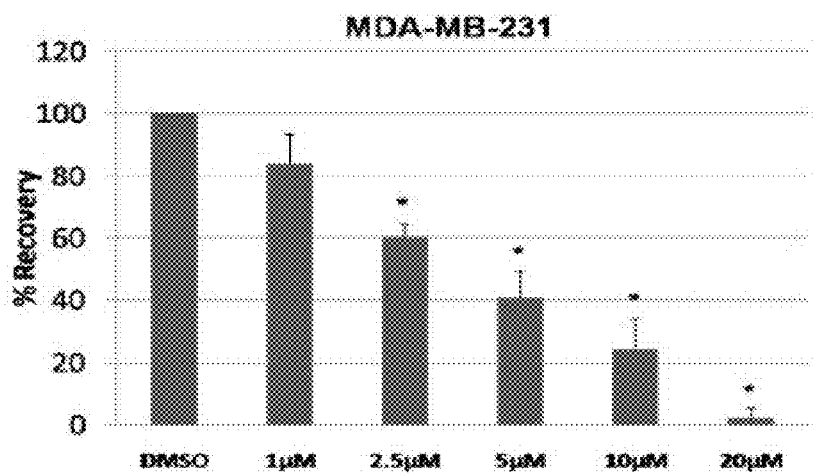
Figure 6C:
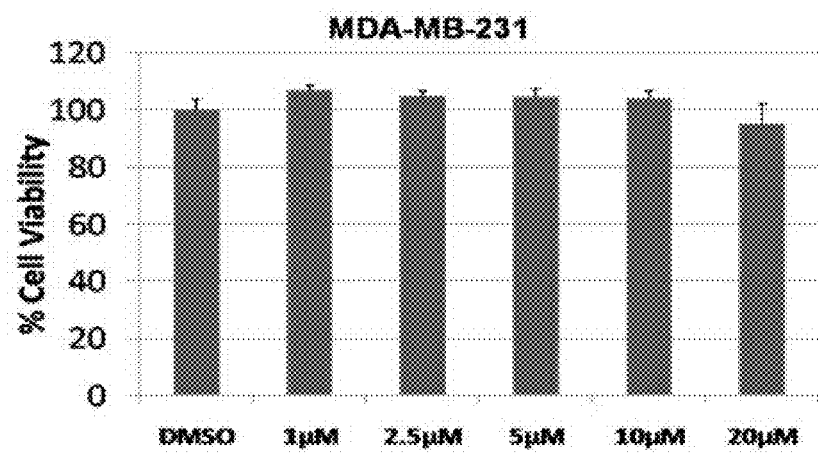

Cell migration is important in physiologic processes, such as wound healing and tumor metastasis. To assess the affect of LLL12 on cell migration a wound-healing assay was done. Following the creation of a wound, cells were treated with various concentrations of LLL12. The treatment was removed after 4 h. Cells were allowed to migrate into the denuded area for 24 h. Treatment with LLL12 at a concentration of 2.5 µM or higher caused a significant decrease in cell migration (FIG. 6B). The ability of LLL12 to inhibit cell migration may not be due to its ability to inhibit cell proliferation. MTT assay reveals that the dosages and time points used in the migration assay have minimal impact on cell viability (FIG. 6C).

Quantitative Combinatorial Effects Between LLL12 and Doxorubicin or Gemcitabine.

Figure 7A:
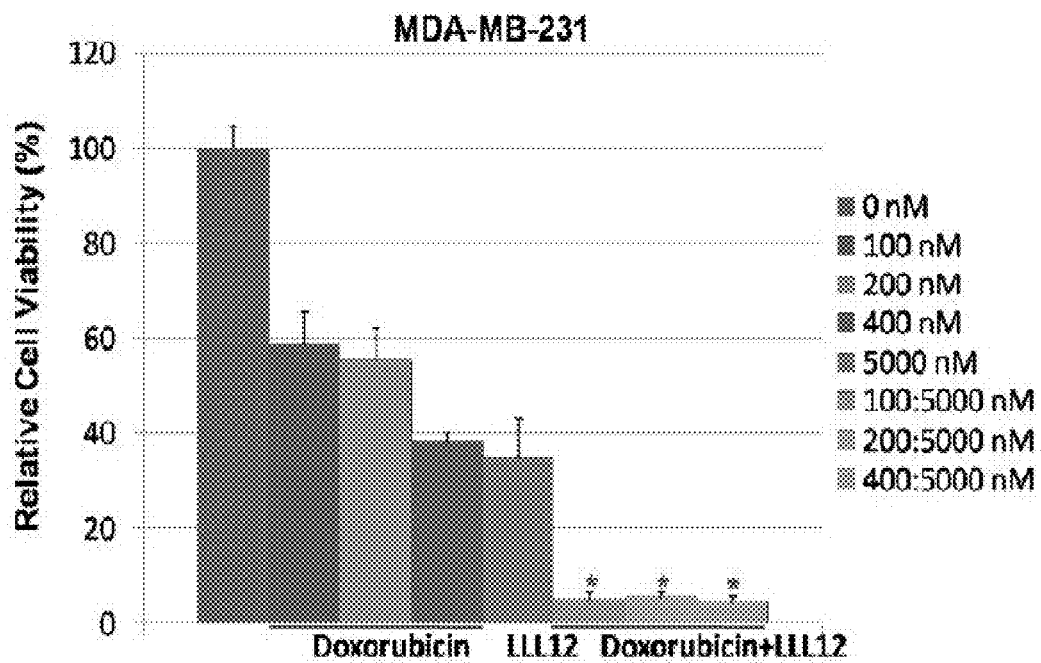
FIGS. 7A-7B. The combinatorial effect of LLL12 and chemotherapy drugs, doxorubicin and gemcitabine.
Figure 7B:
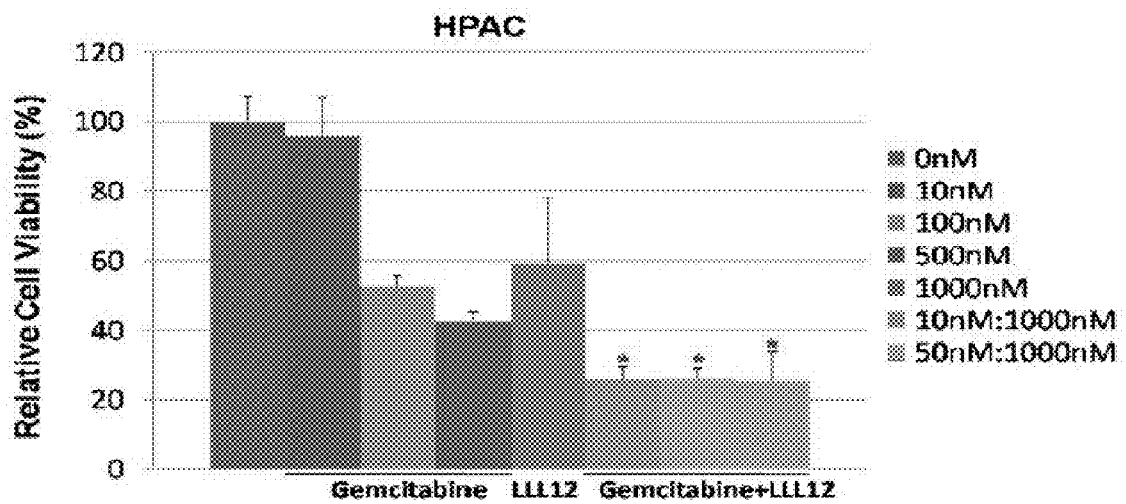

The inventors evaluated the potential of LLL12 to act in a synergistic manner with doxorubicin or gemcitabine. MDA-MB-231 breast cancer cells were treated with doxorubicin or LLL12. HPAC pancreatic cancer cells were treated with gemcitabine or LLL12. The treatments lead to a dose dependent decrease of cellular viability. To determine the combinatorial effects of the treatments, a constant concentration of LLL12 was used with varying concentrations of doxorubicin or gemcitabine. Following 72 h of treatment, a greater decrease in cell viability is seen in the combination treatments (FIGS. 7A and 7B). The Combinational Index (CI) for each drug and concentration combination was calculated. The CI value of all the combinations of treatments were less than 1, indicating synergism between LLL12 and doxorubicin or gemcitabine. The synergistic effects seen with LLL12 and currently used cancer therapeutic agents could prove useful in cancer therapy.

Effect of the Expression of Constitutively Active STAT3 Protein on LLL12-Mediated Inhibition.

Figure 8A:
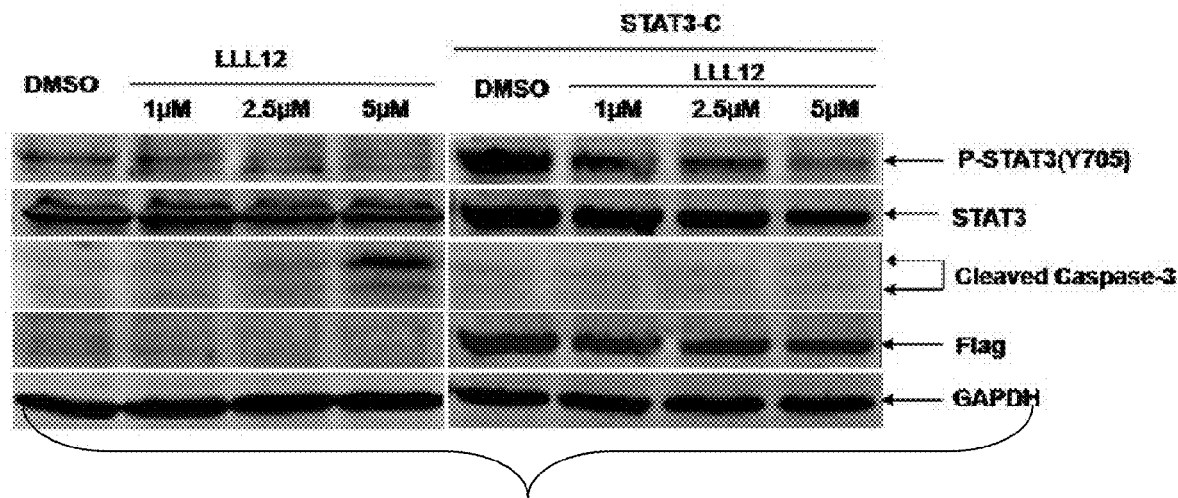
FIGS. 8A-8B. The effect of STAT3-C expression on LLL12-mediated inhibition in U87 glioblastoma cells. Cells were transfected with a vector expressing constitutively active STAT3, STAT3-C, for 24 hours, then treated with LLL12 for another 24 hours.
Figure 8B:
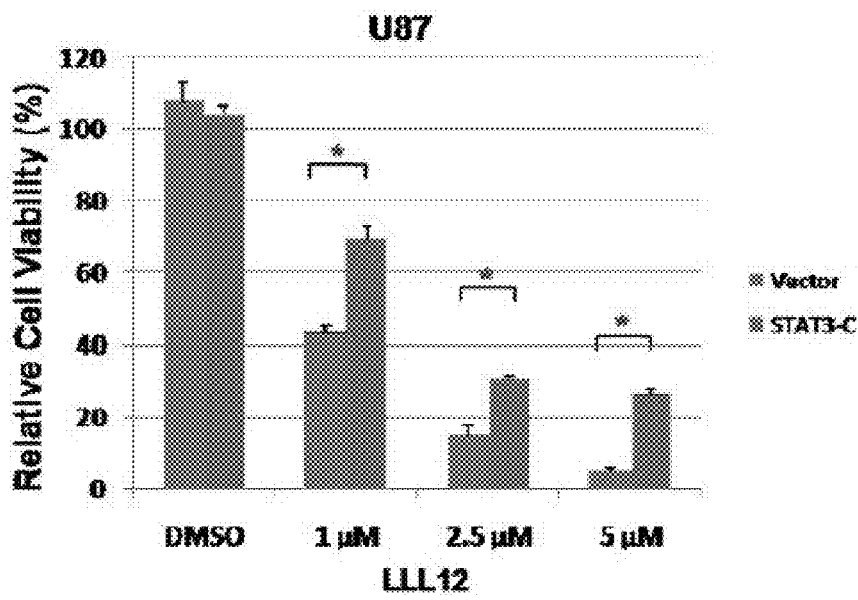

To confirm LLL12 inhibition is indeed through the inhibition of STAT3, U87 gliobalstoma cells were transfected with a constitutively active form of STAT3, STAT3-C (a murine STAT3). LLL12 (2.5 and 5 µM) inhibited STAT3 phosphorylation at Tyr 705 and induced apoptosis which was indicated by capase-3 cleavage in U87 cells (FIG. 8A). However, LLL12 did not increase cleaved caspase-3 after the U87 cells were transfected with STAT3-C expression vector (FIG. 8A). The expression of Flag-STAT3 was verified in STAT3-C-transfected U87 but not in non-transfected U87 cells (FIG. 8A). The inhibition of cell viability of LLL12 in U87 cells was also partially reversed by the transfection with STAT3-C expression vector (FIG. 8B). The results show that STAT3-C can at least partially rescue LLL12-mediated inhibition. The fact that the inventors did not observe a complete rescue by STAT3-C, may be due to the transfection efficiency. Not 100% of U87 cells were transfected and cells did not express STAT3-C are still sensitive to LLL12 inhibition.

LLL12 Suppresses Tumor Growth in Mouse Model In Vivo.

Figure 9A:
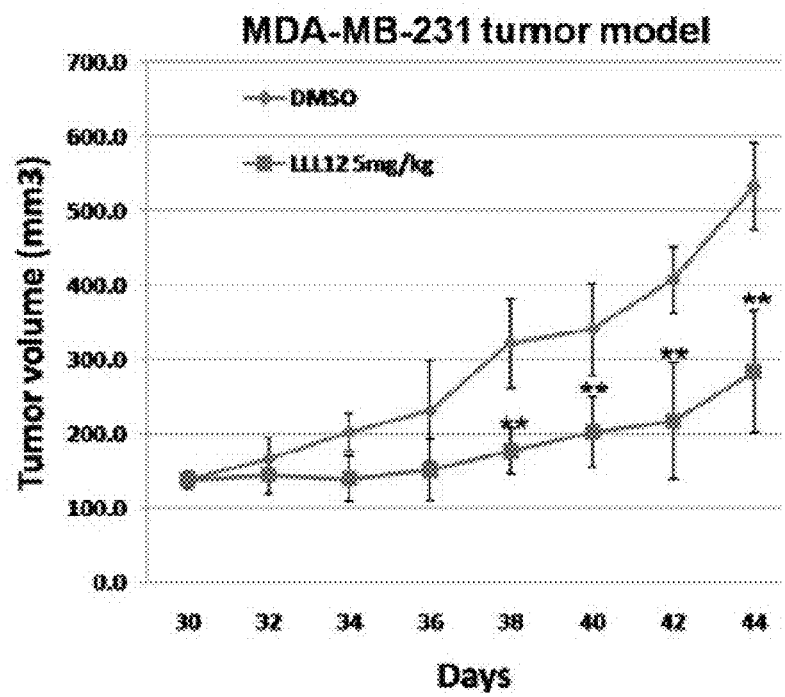
Figure 9B:
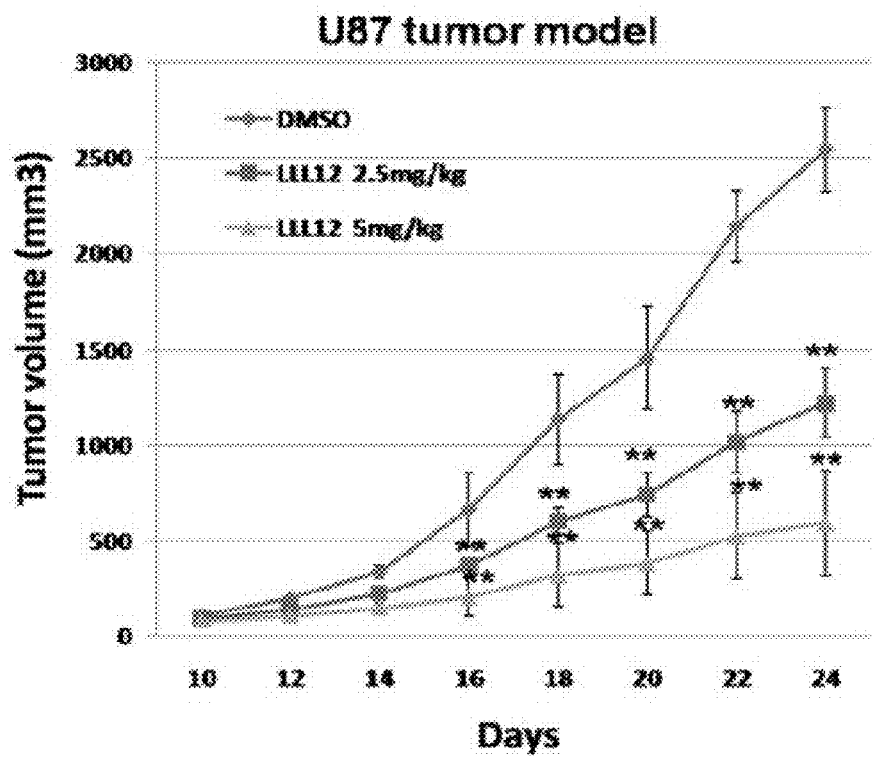

The inventors further investigated whether LLL12 exhibits anti-tumor effect in vivo. Mouse xenograft experiments were performed by implanting MDA-MB-231 breast cancer cells or U87 glioblastoma cell line and then giving 2.5 and 5 mg/kg LLL12 or DMSO daily after tumor development. As shown in FIG. 9, LLL12 significantly inhibited tumor growth compared with DMSO-treated controls in the MDA-MB-231 (FIG. 9A) and U87 xenografted mice (FIG. 9B). STAT3 but not ERK1/2 phosphorylation of tumor tissue samples from these mice were also decreased by LLL12 (FIG. 9C) suggesting that inhibition of STAT3 resulted in the suppression of tumor grow in mice.

Compound Assessments for Drug-Likeness.

Drug-likeness characteristics of LLL12 were evaluated using QikProp (Schrodinger LLC). The absorption, distribution, metabolism, excretion, and toxicity (ADME/Tox) of LLL12 were computed. Fifty "drug-likeness" parameters were evaluated, including molecular weight, polarity, solubility, cell permeability, blood brain barrier, HERG K+ blockage, HSA binding, metabolic stability, and more. LLL12 showed decent "druglike" properties. Selected highlights are listed here: (1) possible in vivo metabolic reactions range only from 1 to 3; (2) composite log P values range from −2 to 2; (3) predicted IC50 values for HERG K+ channels are around −3, well above −5 for any concern; (4) predicted Caco-2 and MCDK cell permeability values are acceptable; (5) predicted brain/blood partition coefficients are above −3; (6) predicted index of binding to human serum albumin ranges from −0.5 to −0.8, well within recommended range of −1.5-1.5; (7) predicted human oral absorption percentage is around 60%. Compared to existing drugs, LLL12 is 90% similar to Sulfacytine and Chlorthalidone.

Breast Cancer Initiating Cells.

This invention demonstrates that elevated STAT3 phosphorylation is expressed in breast cancer initiating cells. The results demonstrate that STAT3 is a novel therapeutic target in breast cancer initiating cells and that inhibition of activated STAT3 in cancer initiating cells offers a more effective treatment for breast carcinoma.

At the present time, the main effort to target constitutive STAT3 signaling is only focused on the bulk of cancer cells. To date, no report has been published that targets STAT3 in breast cancer and other cancer stem cells except in glioblastoma cells. ALDH1 was confirmed to be a new marker of breast cancer stem cells and a predictor of poor clinical outcome. These results demonstrate, for the first time, that the $ALDH^+$ and $ALDH^+/CD44^+/CD24^-$ subpopulations of breast cancer cells expresses higher levels of STAT3 phosphorylation compared to the un-separated, $ALDH^-$, or $ALDH^-/CD44^+/CD24^-$ subpopulation of breast cancer cells. The results also show that there is a significant correlation between the nuclear staining of STAT3 phosphorylation and the expression of ALDH in the clinical breast cancer tissues from cancer patients. These results demonstrate that constitutive STAT3 signaling is a novel therapeutic target in breast cancer initiating cells.

To explore the inhibition of STAT3 in breast cancer stem cells, the inventors examined the inhibitory effects of two STAT3 inhibitors, LLL12 and Stattic as well as STAT3 ShRNA.

LLL12 is a Novel and More Potent Derivative of LLL3.

The results show that LLL12 is potent in inhibiting STAT3 phosphorylation, cell viability, and the formation of tumorspheres, and inducing apoptosis in the $ALDH^+$ subpopulation of breast cancer cells from MDA-MB-231, SUM159, and SK-BR-3. Stattic can also inhibit cell viability and the formation of tumorspheres in the $ALDH^+$ subpopulation of breast cancer cells from MDA-MB-231, SUM159, and SK-BR-3. However, it is less potent than LLL12, an observation which is consistent with weaker predictive binding affinity to STAT3 than LLL12. In addition, STAT3 ShRNA also inhibits STAT3 phosphorylation and cell viability in $ALDH^+$ cells. LLL12 can also down-regulate putative STAT3 or IL-6 downstream target genes in $ALDH^+$ subpopulation that are involved in stem cell growth and survival such as Notch 1 and Notch 3 as well as known STAT3 downstream target genes, such as Cyclin D1, survivin, Bcl-2, Bcl-XL, MMP-2, and MMP-9 that are involved in proliferation and survival.

This Invention Provides Molecular Mechanisms of LLL12-Mediated Inhibition of STAT3 in Breast Cancer Initiating Cells.

The inventors have also examined the effects of STAT3 inhibition by LLL12, Stattic, and STAT3 ShRNA on the $ALDH^-$ subpopulation. All of them show some inhibitory effects. However, this may be due to $ALDH^-$ cells still express certain levels of STAT3 phosphorylation and is only slightly lower or little difference from the un-separated cells (although is lower than $ALDH^+$ cells). Since the un-separated MDA-MB-231, SUM-159, and SK-BR-3 breast cancer cells are known to be sensitive to STAT3 inhibitors, ALDH cells, which may contain slightly more differentiated cancer stem cells, should also be sensitive to the inhibition by STAT3 inhibitors, LLL12, Stattic, as well as STAT3 ShRNA. These results show that STAT3 inhibitors, LLL12 and Statttic may eliminate both ALDH+ and ALDH− subpopulations of breast cancer cells.

The results also show that constitutive active STAT3 in these cancer initiating cells enhances tumor growth in mice, whereas STAT3 blockade by LLL12 directly suppressed MDA-MB-231 and SUM-159 $ALDH^+$ cell growth in xenograft and mammary fat pad mouse models respectively in vivo. Furthermore, LLL12 also suppress the SUM-159 $ALDH^+/CD44^+/CD24^-$ cell growth in mouse xenograft tumor model in vivo. These in vivo results were consistent with the in vitro cancer initiating cell data using LLL12, indicating that LLL12 is a potent STAT3 inhibitor in the suppression of tumor growth of breast cancer initiating cells in the mouse model in vivo.

In Vitro Methods:

The present invention also provides in vitro methods for selectively inhibiting STAT3 activation, cell growth, proliferation and migration arrest and/or apoptosis of cancer cells, by contacting the cells with an effective amount of a composition containing a Compound herein, or a pharmaceutically acceptable salt or hydrate thereof. Competitive assays using the present compounds, tissue localization assays, toxicology screens, etc. using the presently-invented compounds, compositions, formulations, etc. are within the scope of the present invention.

Although the methods of the present invention can be practiced in vitro, it is contemplated that the preferred embodiments for the methods comprise contacting the cells in vivo, i.e., by administering the compounds to a subject harboring cancer cells in need of treatment.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified. Data are presented as Mean±SEM and compared using Student's t-test. Significance was accepted at $p<0.05$.

EXAMPLES

Example 1

Synthesis of the Present Compounds

Figure 1B:
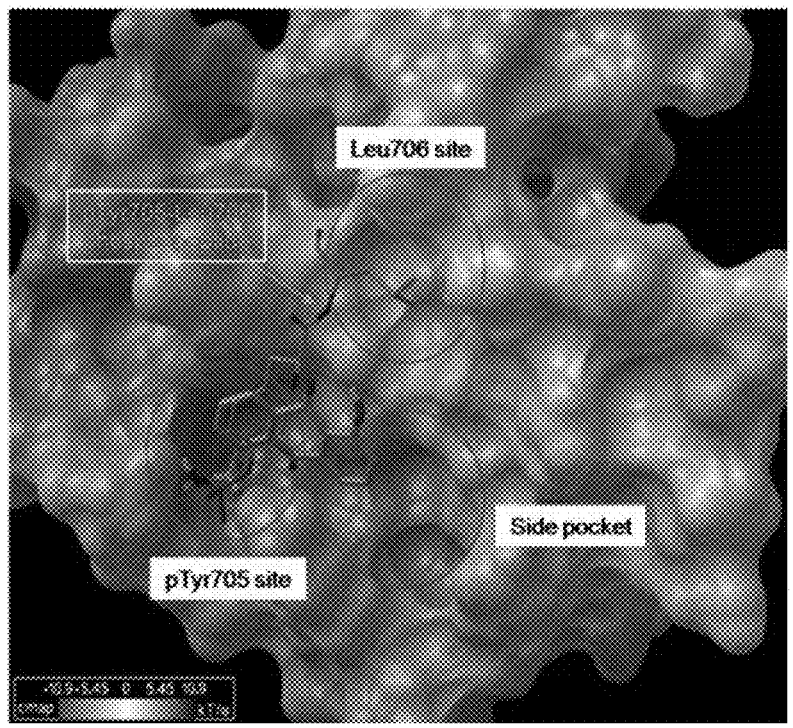

The structure and synthesis of LLL12 is shown in FIG. 1A. To optimize potency and selectivity, the main scaffold of LLL12 was designed to contain fragments that directly contact the pY705 binding site of STAT3 (FIG. 1B). A simulated docking model showed that the sulfonamide tail of LLL12 occupies the pY705-binding pocket of STAT3 with at least three hydrogen bonds. A computer-simulated binding energy of LLL12 to STAT3 was −7.8 Kcal/mol.

Chemicals and Reagents:

Chemicals (except 3-Hydroxy-2-pyrone, which was purchased from Tyger Scientific, Ewing, N.J.) and silica gel were purchased from Sigma-Aldrich Chemical Co. (Milwaukee, Wis.). The chemicals were checked for purity by TLC and nuclear magnetic resonance. Melting points were determined on a Thomas Hoover capillary melting point apparatus and were uncorrected. Proton nuclear magnetic resonance spectra were obtained with a Bruker Anance 300 (300 MHz) spectrophotometer (Bilerica, Mass.).

Synthesis of Compound 2:

Naphthalene sulfonyl chloride (compound 1) (1 g, 4.41 mmol) was dissolved in acetone (52 ml) and was stirred at 0°

C. for 30 mins. Ammonium hydroxide (52 ml) was cooled to 0° C. and was added to the above mixture and stirred at room temperature for 3 hrs. The acetone was then removed at reduced pressure. The residue was dissolved in dichloromethane (100 ml) and washed with water (2×100 ml). The organic layer was collected and evaporated under reduced pressure. The residue was purified by silica column chromatography (hexane/EtOAc, 3:1) yielding compound 2 (750 mg, 82.1%); m.p 147-149° C. (lit. 150° C.).

Synthesis of Compound 3:

Compound 2 (500 mg, 2.41 mmol) was dissolved in glacial acetic acid (5.0 ml). Chromium trioxide (1.08 g, 10.85 mmol) was dissolved in a mixture of water/glacial acetic acid (1:1, 2 ml) and added to the solution of compound 2 in glacial acetic acid and was stirred under reflux for 15 mins. The solution was cooled to 0° C. and water (25 ml) was added and the resulting solution was stirred overnight at room temperature. The reaction mixture was diluted with water (500 ml) and extracted with ether (3×100 ml). The organic layer was collected and dried under reduced pressure and purified with silica column chromatography ethyl acetate/hexane (2:3) to yield compound 3 (88 mg, 15.4%); m.p (187-188° C.); 1H NMR (300 MHz, DMSO) δ 7.23 (2H, d, J=9 Hz), 7.43 (2H, S), 8.11 (1H, t, J=9 Hz), 8.34 (1H, d, J=9 Hz), 8.515 (1H, d, J=9 Hz). ([M+Na]$^+$ 260.7).

Synthesis of LLL12:

A solution of compound 3 (200 mg, 0.843 mmol) in Chloroform (14 ml) was stirred at −20° C. for 10 mins followed by the addition of triethylamine (0.01 ml) and stirring continued at −20° C. for an additional 15 mins. 3-Hydroxy-2-pyrone (compound 4) (86 mg, 0.767 mmol) dissolved in chloroform (1 ml) was added to the reaction mixture and stirred at room temperature for 1 hr. The solvent was removed under reduced pressure. The resulting residue was diluted with water (50 ml) and the aqueous solution was extracted with ethyl acetate (3×50 ml). The organic layer was separated, dried (brine) and evaporated. The crude product was purified by silica column chromatography (hexane/EtOAc, 4:1) yielding LLL12 (50 mg, 20%). m.p (179-181° C.); 1H NMR (300 MHz, DMSO) δ 7.42-7.85 (5H, m), 8.11 (1H, m), 8.56 (2H, m), 12.05 (1H, s). Mass spectrometry ([M+Na]$^+$ 326.1).

The synthesis of LLL12 began with the reaction of sulfonyl chloride 1 with ammonium hydroxide to form 2. Oxidation of 2 yielded the naphthoquinone 3 with chromium (VI) oxide. Base-catalyzed Diels-Alder reactions of 3-hydroxy-2-pyrone 4 with compound 3 at −20° C. yield LLL12 and is regioisomer in a ratio of 98:2.

Example 2

LLL12 Inhibits STAT3 Phosphorylation and Induces Apoptosis in Human Breast and Pancreatic Cancer Cells and Glioblastoma Cells LLL12 was evaluated for its effect on breast cancer cells (MDA-MB-231 and SK-BR-3), pancreatic cancer cells (HPAC and PANC-1), and glioblastoma cells (U87 and U373) which express elevated levels of STAT3 phosphorylation.

Human breast cancer cell lines (MDA-MB-231, MDA-MB-453, and SK-BR-3), human pancreatic cancer cell lines (HPAC and PANC-1), glioblastoma cell line (U87), human hepatocytes (HH), and normal human lung fibroblasts (WI-38) were purchased from the American Type Culture Collection. Human glioblastoma cell line (U373) was kindly provided by Dr. Sean Lawler (The Ohio State University). Human mammary epithelial cells (HMEC) were purchased from Lonza Walkersville, Inc. (Walkersville, Md.) and maintained in Ham's F12 Medium (Mediatech) supplemented with 5 μg/mL insulin, 1 μg/mL hydrocortisone, 10 μg/mL epidermal growth factor, 100 μg/mL cholera toxin, 5% Fetal Bovine Serum (FBS). Immortalized human Pancreatic Duct Epithelial (HPDE) cells were provided by Dr. Ming-Sound Tsao at the University of Toronto and maintained in CnT-07CF epidermal keratinocyte medium (CELLnTEC Advanced Cell Systems, Bern, Switzerland) supplemented 0.07 mM $CaCl_2$. The human hepatocytes (HH) were maintained in Hepatocyte Medium (ScienCell) plus hepatocyte growth supplement and 5% FBS. All other cell lines were maintained in Dulbecco's Modified Eagle Medium supplemented with 10% FBS, 4.5 g/L L-glutamine, sodium pyruvate, and 1% penicillin/streptomycin. All cell lines were stored in a humidified 37° C. incubator with 5% $CO_2$.

Human breast cancer cell lines (MDA-MB-231 and SK-BR-3), human pancreatic cancer cell lines (HPAC and PANC-1), human glioblastoma cell lines (U87 and U373), and human normal cells lines (HPDE, HMEC, HH, and WI-38) were treated with LLL12 (5 μM or 10 μM) or DMSO at 60-80% confluence in the presence of 10% FBS for 24 hours, then lysed in cold RIPA lysis buffer containing protease inhibitors and subjected to SDS-PAGE. Membranes were probed with a 1:1000 dilution of antibodies (Cell Signaling Tech.) against phospho-specific STAT3 (Tyrosine 705), phospho-specific ERK1/2 (Threonine 202/Tyrosine 204), phospho-specific Src (Tyrosine 416), phospho-specific mTOR (Serine 2448), cleaved Poly (ADP-ribose) polymerase (PARP), cleaved caspase-3, cyclin D, Bcl-2, survivin, and GAPDH. Membranes were analyzed using enhanced chemiluminescence Plus reagents and scanned with the Storm Scanner (Amersham Pharmacia Biotech Inc, Piscataway, N.J.).

LLL12 inhibited STAT3 phosphorylation at tyrosine residue 705 (Tyr 705) in all six cancer cell lines (FIGS. 2A-D, FIG. 10). LLL12 was not found to inhibit phosphorylation of other kinase, such as ERK1/2, mTOR, and Src, indicating selectivity for STAT3. As shown in FIGS. 2A-D, downstream targets of STAT3, such as cyclin D1, survivin, and Bcl-2, were down regulated by LLL12.

Without being bound by a particular theory, the inhibition of STAT3 phosphorylation by LLL12 seems consistent with the induction of apoptosis as evidence by the cleavages of PARP and caspase-3 (FIGS. 2A-D, FIG. 10). The effect of LLL12 was also examined in cells that do not express elevated levels of STAT3 phosphorylation [human Pancreatic Duct Epithelial (HPDE) cells, human Mammary Epithelial cells (HMEC), human hepatocytes (HH), and WI-38 normal lung fibroblasts]. LLL12 did not induce cleaved PARP or caspase-3 in any of these cells lines (FIG. 2E). This indicates that LLL12 is selective for cancer cells expressing elevated levels of STAT3 phosphorylation.

Example 3

LLL12 Inhibits STAT3 Phosphorylation Induced by IL-6

Activation of STAT3 can be induced by IL-6. MDA-MB-453 breast cancer cells, which do not express persistently phosphorylated STAT3, were used to determine if LLL12 is capable of inhibiting IL-6 induced STAT3 phosphorylation. The results of this study were that IL-6 stimulates STAT3 phosphorylation in MDA-MB-453 cells. This stimulation of STAT3 phosphorylation was blocked by LLL12 in a dose-dependent manner (FIG. 3). These results support that LLL12 is a potent inhibitor of STAT3 phosphorylation in cancer cells.

MDA-MB-453 breast cancer cells were seeded in 10 cm plates and allowed to adhere overnight. The following night, the cells were serum starved. The cells were then left untreated or were treated with LLL12 (0.5 µM-2 µM) or DMSO. After 2 hours the untreated and LLL12 treated cells were stimulated by IL-6 (25 ng/mL). The cells were harvested at 30 min and analyzed by western blot.

Example 4

LLL12 Inhibits STAT3 DNA Binding

Figure 4D:
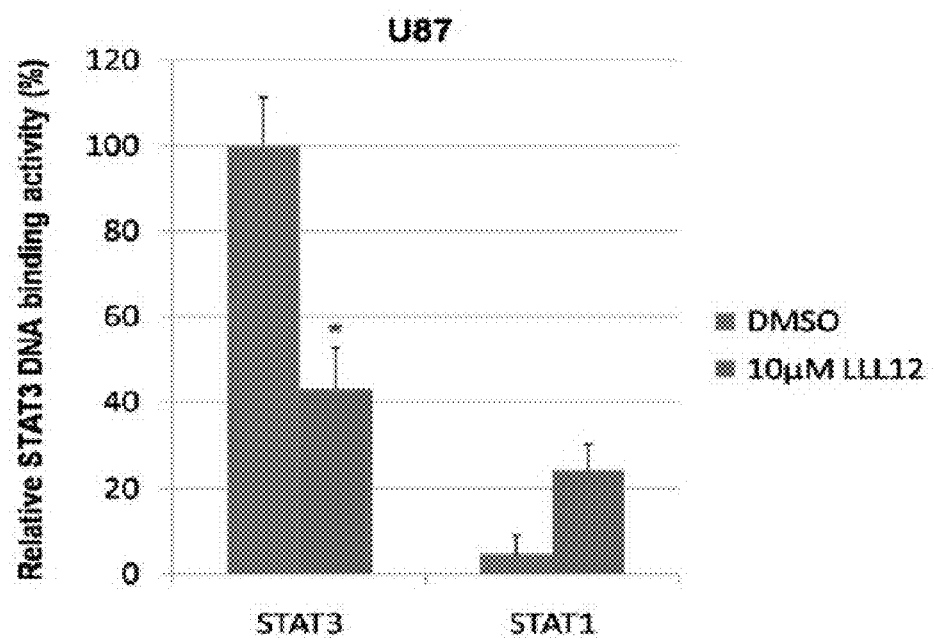

To confirm the inhibition of STAT3 signaling by LLL12, inhibition of STAT3 DNA binding activity was examined. LLL12 caused a statistically significant inhibition of STAT3 DNA binding activity in breast cancer cell lines, SK-BR-3 (FIG. 4A) and MDA-MB-231 (FIG. 4B), pancreatic cancer cell line, HPAC (FIG. 4C), and glioblastoma cell line, U87 (FIG. 4D).

Example 5

LLL12 Did not Inhibit STAT1 DNA Binding Activity (FIGS. 4B and 4D), Indicating a Specificity of LLL12 for STAT3 over STAT1

MDA-MB-231, SK-BR-3, HPAC, and U87 cancer cells at 60-80% confluence were treated with LLL12 (5 µM or 10 µM) or DMSO in the presence of 10% FBS for 24 hours. A nuclear extract kit (Clontech Inc.) was used to obtain nuclear extracts. The nuclear extracts were analyzed for STAT3 and/or STAT1 DNA binding activity using a STAT3 or STAT1 Transcription Factor Kits (Clontech Inc.), which provide an ELISA-based method to detect DNA binding by transcription factors.

Example 6

LLL12 Inhibits STAT3-Dependent Transcriptional Activities and Transcription of Downstream Targets of STAT3

STAT3 binding to the promoters of the target genes induces the transcription of several proliferation and anti-apoptotic associated proteins. STAT3-dependent transcriptional luciferase activity was then examined after treating with LLL12 for 24 hours. As seen in the luciferase assay (FIG. 5A), LLL12 also inhibited STAT3-dependent transcriptional activity in a dose-dependent manner. To further analyze the impact of LLL12 on the inhibition of STAT3 transcription of downstream target genes of STAT3 by reverse transcriptase PCR was studied. MDA-MB-231 breast cancer cells, HPAC pancreatic cancer cells and U373 glioblastoma cells were treated with LLL12 (5 or 10 µM) or DMSO for 24 hours. Reverse Transcriptase PCR was run for cyclin D1, survivin, and Bcl-XL. Treatment with LLL12 resulted in an inhibition of the transcription of STAT3-regulated genes (FIG. 5B).

STAT3-dependent transcriptional luciferase activity was measured using MDA-MB-231 cloned cells that stably integrate the STAT3-dependent luciferase reporter construct, pLucTKS3. The cells were grown in 6-well plates until semi-confluent and treated in 5% FBS with LLL12 (1 µM-10 µM) or DMSO for 24 hours. The luciferase assay (Promega, Madison, Wis.) was run according to the manufacturer's protocol. The STAT3 luciferase activity of the LLL12 treated cells is reported relative to pLucTKS3-transfected cells treated with DMSO arbitrarily set at 100%.

Reverse Transcriptase-Polymerase Chain Reaction (RT-PCR)

MDA-MB-231, HPAC, and U373 cells were treated with LLL12 (5 or 10 µM) or DMSO at 60-80% confluence in the presence of 10% FBS for 24 hours. RNA from the cells was then collected using Uneasy Kits (Qiagen). Primer sequences and source information of STAT3 downstream target genes can be found in supplemental data Table 1. PCR amplification was done under the following conditions: 5 min at 94° C. followed by 25 cycles of 30 seconds at 94° C., 30 sec at 55° C., and 30 seconds at 72° C. with a final extension of 5 min at 72° C.

TABLE 1

The DNA sequences of primers of STAT3 downstream target genes (cyclin D1, survivin, Bcl-xl and Bcl-2) used for RT-PCR analysis.

| Gene | Primers | Size | SEQ ID NO: |
|---|---|---|---|
| Cyclin D1 | Forward: 5'-GCTGGAGCCCGTGAAAAAGA-3' | 247 | 1 |
| | Reverse: 5'-CTCCGCCTCTGGCATTTTG-3' | | 2 |
| Survivin | Forward: 5'-ACCAGGTGAGAAGTGAGGGA-3' | 309 | 3 |
| | Reverse: 5'-AACAGTAGAGGAGCCAGGGA-3' | | 4 |
| Bcl-2 | Forward: 5'-TCTTTGAGTTCGGTGGGGTC-3' | 304 | 5 |
| | Reverse: 5'-TGCATATTTGTTTGGGGCAGG-3' | | 6 |
| Bcl-XL | Forward: 5'-TTGGACAATGGACTGGTTGA-3' | 765 | 7 |
| | Reverse: 5'-GTAGAGTGGATGGTCAGTG-3' | | 8 |
| GAPDH | Forward: 5'-TGATGACATCAAGAAGGTGGTGAAG-3' | 240 | 9 |
| | Reverse: 5'-TCCTTGGAGGCCATGTGGGCAT-3' | | 10 |

Example 7

Inhibition of Cell Proliferation/Viability in Human Breast and Pancreatic Cancer Cells and Glioblastoma Cells by LLL12

STAT3 activation is important for tumor cell proliferation and survival. Cell viability assays were run to examine the inhibitory affect of LLL12 on human breast and pancreatic cancer cells and glioblastoma cell proliferation and survival. A dose-dependent inhibition in tumor cell proliferation/viability was seen after 72 hours of treatment. IC50 values were calculated for LLL12 and other previously characterized inhibitors (Table 2); WP1066, a JAK2/STAT3 inhibitor, and S3I-201, a STAT3 inhibitor. The inhibitory efficacy of the three compounds was compared. LLL12 is substantially more potent in the inhibition of cell viability than the other available inhibitors in all the cell lines analyzed.

LLL12, a STAT3 inhibitor, and WP1066, a JAK2 inhibitor, were synthesized in Dr. Pui-Kai Li's laboratory (College of Pharmacy, The Ohio State University). The powder was dissolved in sterile dimethyl sulfoxide (DMSO) to make a 20 mM stock solution. Aliquots of the stock solution were stored at −20° C. S3I-201, a STAT3 SH2 inhibitor, was purchased from Calbiochem.

TABLE 2

The half-maximal inhibitory concentrations (IC$_{50}$) (µM) obtained for STAT3 inhibitors in human breast and pancreatic cancer and glioblastoma.

|  | LLL12 | WP1066 | S3I-201 |
|---|---|---|---|
| MDA-MB-231 | 0.97 | 7.48 | >100 |
| SK-BR-3 | 3.09 | 3.31 | >100 |
| PANC-1 | 0.29 | 5.12 | >100 |
| HPAC | 0.16 | 2.52 | >100 |
| U87 | 0.21 | 5.78 | 55.10 |
| U373 | 0.86 | 5.16 | 52.50 |

Example 8

Anchorage Independence and Cell Viability

An indicator of transformation is the ability of cells to grow in the absence of substratum attachment. Anchorage independent growth is vitally important in the formation of the tumor. The soft agar colony formation assay provides an assessment of tumor cells susceptibility to a drug in an anchorage independent environment. It is considered a more sensitive measure of toxicity, reflecting the efficacy of a drug, because it is analyzed when cells are in a proliferative state. The effect LLL12's ability to inhibit STAT3-associated colony formation of MDA-MB-231 cells in soft agar was studied. Compared to the DMSO control, treatment with LLL12 led to a decrease of over 95% in colony formation (FIG. 6A). The results of this assay further confirm what was seen in the MTT assay, LLL12 is a potent inhibitor for cancer cell viability.

Human breast cancer cell lines (MDA-MB-231 and SK-BR-3), human pancreatic cancer cell lines (PANC-1 and HPAC), glioblastoma cell lines (U87 and U373) were seeded in 96-well plates at a density of 3,000 cells per well. Different concentration of LLL12 (0.1-1004), WP1066 (1-10 µM), or S3I-201(1-100 µM) were added in triplicate to the plates in the presence of 10% FBS. The cells were incubated at 37° C. for a period of 72 hours. 3-(4,5-Dimethylthiazolyl)-2,5-diphenyltetrazolium bromide (MTT) viability assay was done according to manufacturer's protocol (Roche Diagnostics, Mannheim, Germany). The absorbance was read at 595 nm. Half-maximal inhibitory concentrations (IC50) were determined using Sigma Plot 9.0 Software (Systat Software Inc., San Jose, Calif.).

A base 0.6% agar gel with 10% FBS in DMEM was prepared and added to the wells of a 6-well culture dish. MDA-MB-231 breast cancer cells were plated at a density of 5,000 cells per well on-top of the base agar for anchorage independent growth analysis in 0.4% agar gel with 10% FBS in DMEM supplemented with LLL12 (1 µM or 5 µM) or DMSO. The cells were maintained at 37° C. and allowed to grow for two weeks. The colonies were stained using MTT dye (100 µL per well). Pictures of the colonies were taken using a Leica MZ 16FA inverted microscope (Leica Microsystems) with a 7.4 Slider Camera (Diagnostic Instruments Inc.). The colonies were scored by counting and numbers were normalized as a percentage of colonies formed in DMSO.

Example 9

LLL12 Inhibits Cell Migration in MDA-MB-231 Breast Cancer Cells

Cell migration is important in physiologic processes, such as wound healing and tumor metastasis. To assess the affect of LLL12 on cell migration a wound-healing assay was done. Following the creation of a wound, cells were treated with various concentrations of LLL12. The treatment was removed after 4 h. Cells were allowed to migrate into the denuded area for 24 h. Treatment with LLL12 at a concentration of 2.5 µM or higher caused a significant decrease in cell migration (FIG. 6B). Without being bound by any particular theory, this study implies that the ability of LLL12 to inhibit cell migration may not be due to its ability to inhibit cell proliferation. MTT assay reveals that the dosages and time points used in the migration assay have minimal impact on cell viability (FIG. 6C).

MDA-MB-231 breast cancer cells (3×10$^5$ per well) were seeded in a six-well plate. Approximately 24 hours later, when the cells were 100% confluent, the monolayer was scratched using a 1 mol pipette tip, and washed once to remove non-adherent cells. New medium in the presence of 10% FBS containing LLL12 (1-20 µM) or DMSO was added. The treatments were removed after 4 hours and fresh medium was added. After an additional 20 hours without treatment the cells were observed under the microscope. When the wound in the control was closed, the inhibition of migration was assessed by using the ImageJ software, available from the NIH website (http://rsb.info.nih.gov/ij/). The % of wound healed was calculated using the formula: 100−(final area/initial area×100%).

Example 10

Quantitative Combinatorial Effects Between LLL12 and Doxorubicin or Gemcitabine The potential of LLL12 to act in a synergistic manner with doxorubicin or gemcitabine was studied. MDA-MB-231 breast cancer cells were treated with doxorubicin or LLL12. HPAC pancreatic cancer cells were treated with gemcitabine or LLL12. The treatments lead to a dose dependent decrease of cellular viability. To determine the combinatorial effects of the treatments, a constant concentration of LLL12 was used with varying concentrations of doxorubicin or gemcitabine. Following 72 hours of treatment, a greater decrease in cell viability is seen in the combination treatments (FIGS. 7A and 7B). The Combinational Index (CI) for each drug and concentration combination was calculated. The CI value of all the combinations of treatments were less than 1, indicating synergism between LLL12 and doxorubicin or gemcitabine. The synergistic effects seen with LLL12 and currently used cancer therapeutic agents could prove useful in cancer therapy.

MDA-MB-231 breast and HPAC pancreatic cancer cells were seeded in 96-well plates in triplicate at a density of 3,000 cells per well, and treated with LLL12 (500 nM) and Doxorubicin (100-400 nM, Sigma-Aldrich, St. Louis, Mo.), or LLL12 (1000 nM) and gemcitabine (1001000 nM, Sigma-Aldrich, St. Louis, Mo.) in the presence of 10% FBS. LLL12 and Doxorubicin (Sigma-Aldrich, St. Louis, Mo.) or LLL12 and gemcitabine (Sigma-Aldrich, St. Louis, Mo.) synergy with regards to growth inhibition was determined as follows. The log(fa/fu) was plotted against the concentration (D) for each compound alone or in combination, where fa is the fraction affected and fu is the fraction unaffected (1−fa) of cells at each concentration. Calcusyn software (Biosoft, Ferguson, Mo.) was used to determine the combinational index (CI) for each drug and concentration combination. A CI value of less than 1 represents synergism. A CI value equal to 1 represents additive effects. A CI value greater than 1 represents antagonistic effects.

Example 11

Effect of the Expression of Constitutively Active STAT3 Protein on LLL12-Mediated Inhibition

To confirm LLL12 inhibition is indeed through the inhibition of STAT3, U87 glioblastoma cells were transfected with a constitutively active form of STAT3, STAT3-C (a murine STAT3). LLL12 (2.5 and 5 µM) inhibited STAT3 phosphorylation at Tyr 705 and induced apoptosis, as evidenced by capase-3 cleavage in U87 cells (FIG. 8A). However, LLL12 did not increase cleaved caspase-3 after the U87 cells were transfected with STAT3-C expression vector (FIG. 8A). The expression of Flag-STAT3 was verified in STAT3-C-transfected U87 but not in non-transfected U87 cells (FIG. 8A). The inhibition of cell viability of LLL12 in U87 cells was also partially reversed by the transfection with STAT3-C expression vector (FIG. 8B). These results show that STAT3-C can at least partially rescue LLL12-mediated inhibition. The fact that complete rescue by STAT3-C was not observed may be due to the transfection efficiency. Not 100% of U87 cells were transfected, and cells did not express STAT3-C were still sensitive to LLL12 inhibition.

U87 glioblastoma cells were plated in 60-mm³ dishes or 96-well plates. The second day, the cells were transfected using Lipofectamine 2000 (Invitrogen, Carlsbad, Calif.) with a vector encodes the constitutive STAT3 (STAT3-C), which is tagged with FLAG epitope. Cells were treated with LLL12 (1-5 µM) or DMSO twenty four hours after transfection. Twenty four hours later, the cells in 60-mm³ dishes were harvested to run western blot. Cell viability was determined by MTT assay in 96-well plates as described above.

Example 12

LLL12 Suppresses Tumor Growth in Mouse Model In Vivo

The inventors further investigated whether LLL12 exhibits anti-tumor effect in vivo. Mouse xenograft experiments were performed by implanting MDA-MB-231 breast cancer cells or U87 glioblastoma cell line and then giving 2.5 and 5 mg/kg LLL12 or DMSO daily after tumor development. As shown in FIG. 9, LLL12 significantly inhibited tumor growth compared with DMSO-treated controls in the MDA-MB-231 (FIG. 9A) and U87 xenografted mice (FIG. 9B). STAT3 but not ERK1/2 phosphorylation of tumor tissue samples from these mice were also decreased by LLL12 (FIG. 9C) suggesting that inhibition of STAT3 resulted in the suppression of tumor grow in mice.

MDA-MB-231 breast cancer cells ($1 \times 10^7$) and U87 glioblastoma cells ($5 \times 10^6$) were injected (s.c.) into the right flank area of 4- to 5-week-old male athymic nude mice which were purchased from Harlan (Indianapolis, Ind., USA). After tumor development, mice were divided into three treatment groups consisting of 5 mice/group: DMSO vehicle control, 2.5 and 5 mg/kg of LLL12. Tumor growth was determined by measured the length (L) and width (W) of the tumor every other day with a caliper and tumor volume was calculated on the basis of the following formula: volume=$(\pi/6)$ LW². After 14 days of treatments, tumors were harvested from sacrificed mice, snap-frozen in liquid nitrogen and stored in −80° C. Tumors tissue homogenates were lysed and separated by SDS-PAGE to examine the expression of STAT3 phosphorylation in vehicle- and LLL12-treated mice.

Example 13

Breast Cancer Initiating Cell Experiments

Cell Culture

MDA-MB-231 and SK-BR-3 breast cancer cells were acquired from the American Type Culture Collection (Manassas, Va.) and maintained in Dulbecco's Modification of Eagle's Medium supplemented with 10% fetal bovine serum (FBS) (Invitrogen). The SUM159 breast cancer cells were obtained from Dr. Wicha and are commercially available (Asterand, Detroit, Mich.). These three cancer cell lines have been routinely tested and authenticated by the American Type Culture Collection and Asterand respectively. SUM159 cells were cultured in Ham's F12 containing 5% FBS, 5 µg/ml insulin, 1 µg/ml hydrocortisone and 10 ng/ml epidermal growth factor. Because these three breast cancer cell lines express elevated levels of STAT3 phosphorylation, the inventors tested the levels of STAT3 phosphorylation by western blots every three months to make sure they still maintain this oncogenic phenotype and the last time tested was on August 2010. ALDH$^+$ and ALDH$^+$/CD44$^+$/CD24$^-$ cells were grown in a serum-free mammary epithelial basal medium (MEBM) (Clonetics division of Cambrex BioScience) supplemented with B27 (Invitrogen), 20 ng/mL EGF (BD Biosciences), 4 ug/ml Gentamycin (Invitrogen), 1 ng/ml Hydrocortisone (Sigma-Aldrich), 5 µg/ml Insulin and 100 µM beta-mercaptoethanol (Sigma-Aldrich).

Separation of the ALDH$^+$ and ALDH$^+$/CD44$^+$/CD24$^-$ Subpopulations of Breast Cancer Cells.

The ALDEFLUOR kit (StemCell Technologies) was used to isolate the population with high ALDH enzymatic activity as known. Briefly, cells were trypsinized to single cells using 0.05% trypsin and subsequently suspended in ALDEFLUOR assay buffer containing ALDH substrate (BAAA, 1 µmol/l per $1 \times 10^6$ cells) and then incubated for 40 minutes at 37° C. For each sample, an aliquot of cells was stained under identical conditions with 15 mmol/L diethylaminobenzaldehyde (DEAB), a specific ALDH inhibitor, as a ALDH$^-$ control. Anti-human PE-CD24 and PE-Cy5-CD44 antibody (BioLegend) were used for CD44/CD24 identification and to separate ALDH$^+$/CD44$^+$/CD24$^-$ and ALDH$^-$/CD44$^+$/CD24$^+$ cells when combine with ALDH staining. Analysis was performed using a FACStarPLUS (Becton Dickinion) flow cytometer. To assess the effect of STAT3 inhibitors on the subpopulation of ALDH$^+$ cells, ALDH$^+$/CD44$^+$/CD24$^-$ cells, ALDH$^-$/CD44$^+$/CD24$^+$ cells, ALDH$^-$ cells, and un-separated breast cancer cells were treated with 5 µmol/L of LLL12 or 10 µmol/L Stattic for 24 hours; the next day, cells were collected to run the ALDEFLUOR assay.

Tissue microarray slides, Immunohistochemistry, and Immufluorence staining.

Human breast cancer tissue microarray slides were obtained from the Biochain Institute, Inc. containing 95 breast cancer cases. These slides were baked at 60° C. for 1 hour. After deparaffinized, the slides were boiled in a pressure cooker filled with 10 mM Sodium Citrate (PH 6.0) or 1 mM EDTA (PH 8.0), and then subjected to immunohistochemistry or immufluorence staining. Phospho-STAT3 (Tyr705) antibody (1:25; Signaling Technology, Beverly, Mass.) and or ALDH1 (1:100; BD Pharmingen, San Diego, Calif.) were used. For immufluorence, the slides were incubated with both of the primary antibodies and double-stained with Alexa Fluor® 488 conjugated anti-rabbit IgG and Alexa Fluor® 594 conjugated anti-mouse IgG (Cell Signaling Technology, Beverly, Mass.) over night at 4° C. The nuclear were stained with DAPI. Slides were washed and covered.

For immunohistochemistry, endogenous peroxidase activity was quenched by incubated in 3% hydrogen peroxide for 10 min. After blocking, the slides were incubated with primary antibody overnight at 4° C. The Histostain-Plus Kits (Invitrogen, Carlsbad, Calif.) were used as described by manufacturer. Finally, the slides were counterstained with hematoxylin and mounted with CRYSTAL/MOUNT (Biomeda Corp., Foster City, Calif.) for long term preservation. Immuno-stained slides were scored under microscope. The staining intensity was scored on the following scale: 0, no staining; 1, weak staining; 2, moderate staining; and 3, intense staining. Most or all of the cancer tissues showed staining in greater than 50% of area. Scoring of the tissue microarray was completed by two independent researchers. Discrepant scores between the two researchers were rescored to arrive at a single final score. Significance of correlation between phospho-STAT3 and ALDH1 was determined respectively using two-sided Pearson Chi-square ($\chi^2$) test. $p<0.05$ were considered as statistical significance. Statistical analyses were performed using SPSS Version 12.0 software (SPSS, Inc., Chicago, Ill.).

STAT3 Inhibitors

LLL12, a STAT3 inhibitor, was synthesized in one of the inventor's laboratory. The powder was dissolved in DMSO to make a 20 mM stock solution. Stattic, a previously reported STAT3 inhibitor, was purchased from Calbiochem (San Diego, Calif.). Lentivirus short hairpin RNA (ShRNA) that specific targets human STAT3 and control lentivirus that expresses Green Fluorescent Protein (GFP) were provided by Antonio Iavarone at the Columbia University.

Western Blot Analysis

ALDH$^+$ and ALDH$^-$ subpopulations, or ALDH$^+$/CD44$^+$/CD24$^-$ and ALDH$^-$/CD44$^+$/CD24$^+$ subpopulations of breast cancer cells were separated by flow cytometer. After sorting, ALDH$^+$ and ALDH$^+$/CD44$^+$/CD24$^-$ stem cells were cultured in serum-free stem cell medium in ultra-low attachment six-well plates (Corning) to maintain cancer stem cell characteristics. ALDH$^-$, ALDH$^-$/CD44$^+$/CD24$^+$ cells and unseperated cells were cultured in regular medium and replaced with identical stem cell medium for three days before being harvested. To assess the effects of STAT3 inhibitors, ALDH$^+$ and ALDH$^+$/CD44$^+$/CD24$^-$ subpopulations of breast cancer cells were treated with 5 μmol/L of LLL12 for 24 hours. Antibodies (Cell Signaling Tech.) against phospho-specific STAT3 (Tyrosine 705) (P-STAT3, Y705), ERK1/2 (Threonine 202/Tyrosine 204), cleaved Poly (ADP-ribose) polymerase (PARP), cleaved caspase-3, and GAPDH were used for western blots.

Reverse Transcriptase-Polymerase Chain Reaction (RT-PCR)

The ALDH$^+$ and ALDH$^+$/CD44$^+$/CD24$^-$ subpopulations of breast cancer cells was treated with LLL12 (5 μM) or DMSO for 24 h. RNA from the cells was then collected using RNeasy Kits (Qiagen). cDNA was constructed from a 500 ng sample of RNA using Omniscript RT (Qiagen). Primer sequence information can be found in Table 3.

Table 3.

TABLE 3

| Gene | Primers | | Size | SEQ ID NO: |
|---|---|---|---|---|
| Cyclin D1 | Forward: | 5'-GCTGGAGCCCGTGAAAAAGA-3' | 247 | 1 |
| | Reverse: | 5'-CTCCGCCTCTGGCATTTTG-3' | | 2 |
| Survivin | Forward: | 5'-ACCAGGTGAGAAGTGAGGGA-3' | 309 | 3 |
| | Reverse: | 5'-AACAGTAGAGGAGCCAGGGA-3' | | 4 |
| Bcl-2 | Forward: | 5'-TCTTTGAGTTCGGTGGGGTC-3' | 304 | 5 |
| | Reverse: | 5'-TGCATATTTGTTTGGGGCAGG-3' | | 6 |
| Bcl-Xl | Forward: | 5'-TTGGACAATGGACTGGTTGA-3' | 765 | 7 |
| | Reverse: | 5'-GTAGAGTGGATGGTCAGTG-3' | | 8 |
| MMP-2 | Forward: | 5'-GGCCCTGTCACTCCTGAGAT-3' | 474 | 11 |
| | Reverse: | 5'-GGCATCCAGGTTATCGGGGA-3' | | 12 |
| MMP-9 | Forward: | 5'-CGCAGACATCGTCATCCAGT-3' | 409 | 13 |
| | Reverse: | 5'-GGATTGGCCTTGGAAGATGA-3' | | 14 |
| Notch1 | Forward: | 5'-CAACATCCAGGACAACATGG-3' | 229 | 15 |
| | Reverse: | 5'-GGACTTGCCCAGGTCATCTA-3' | | 16 |
| Notch3 | Forward: | 5'-TGTCTTGCTGCTGGTCATTC-3' | 413 | 17 |
| | Reverse: | 5'-CATCTGGGCCACGCACATT-3' | | 18 |
| TWIST1 | Forward: | 5'-GGAGTCCGCAGTCTTACGAG-3' | — | 19 |
| | Reverse: | 5'-TCTGGAGGACCTGGTAGAGG-3' | | 20 |
| ALDH1 | Forward: | 5'-TCCTGGTTATGGGCCTACAG-3' | 237 | 21 |
| | Reverse: | 5'-CTGGCCCTGGTGGTAGAATA-3' | | 22 |
| GAPDH | Forward: 5'-TGATGACATCAAGAAGGTGGTGAAG-3' | | 240 | 9 |
| | Reverse: 5'-TCCTTGGAGGCCATGTGGGCAT-3' | | | 10 |

Tumorsphere Culture

Tumorsphere culture was performed as previously described (4). ALDH$^+$ and ALDH$^+$/CD44$^+$/CD24$^-$ cells were plated as single cells in ultra-low attachment six-well plates at a density of 50,000 viable cells/well. On the second day after seeding, the ALDH$^+$ cancer cells were treated with 2.5-10 μmol/L of LLL12 or Stattic. Tumorsphere growth was observed under a microscope 10 to 15 days later.

Kinase Activity Assay

The possible effects of LLL12 on ten purified human protein kinases were performed at the Millipore UK Limited (Dundee, UK) and Reaction Biology Corp. (Malvern, Pa.) using Kinase profiler assay. The IC50 inhibitory values of LLL12 on the kinase activity were determined using 10 different concentrations of LLL12 with 100 μM as the highest concentration in kinase assays.

MTT Cell Viability Assay

The ALDH$^+$ subpopulation of breast cancer cells was seeded in 96-well plates (3,000 cells/well) in triplicates in a serum-free mammary epithelial basal medium. The following day, cancer cells were treated with 1 to 10 μmol/L of LLL12, Stattic (Calbiochem.) for 72 hours, and STAT3 ShRNA for 48 hours. MTT (Thiazolyl Blue Tetrazolium Bromide, Sigma-Aldrich) assay was used to determine the cell viability.

Mouse Xenograft Tumor Model

All animal studies were conducted in accordance with the principles and standard procedures approved by IACUC at the Research Institute at Nationwide Children's Hospital and the University Committee on the Use and Care of Animals at the University of Michigan. ALDH$^+$ and ALDH$^+$/CD44$^+$/CD24$^-$ subpopulations of MDA-MB-231 and SUM-159 breast cancer cells ($1\times10^5$) respectively were injected (s.c.) into the flank area of female NOD/SCID mice which were purchased from Jackson Laboratory. After tumor development, mice were divided into two treatment groups consisting of 6 mice/group: DMSO vehicle control and 5 mg/kg of LLL12. Tumor growth was determined by measuring the length (L) and width (W) of the tumors and tumor volume was calculated on the basis of the following formula: volume=($\pi$/6) LW$^2$. For mammary fat pad experiments, the inventors injected 1×10$^5$ of sorted SUM159 ALDH$^+$ cells, assessed using Aldefluor kit (StemCell Technologies) in the fat pad of NOD/SCID mice (The Jackson Laboratory), as previously described. 19 days after the cell injection, the inventors randomly assigned mice into two groups with an average volume of approximately 5 mm$^3$ and initiated the treatment. 5 mg/kg of LLL12 (dissolved in 10% DMSO, 18% Cremophor EL and 72% sterile 5% Dextrose) or vehicle alone were administrated i.p. to two groups with for 15 days. Tumors were measured by a caliper every 3 days and the volume was calculated using V=$\pi$(width$^2$×length)/6. After 15 days of treatments, tumors were harvested from euthanized mice, snap-frozen in liquid nitrogen, and stored in −80° C. Tumors tissues were examined for the expression of STAT3 phosphorylation.

Example 14

Figure 11A:
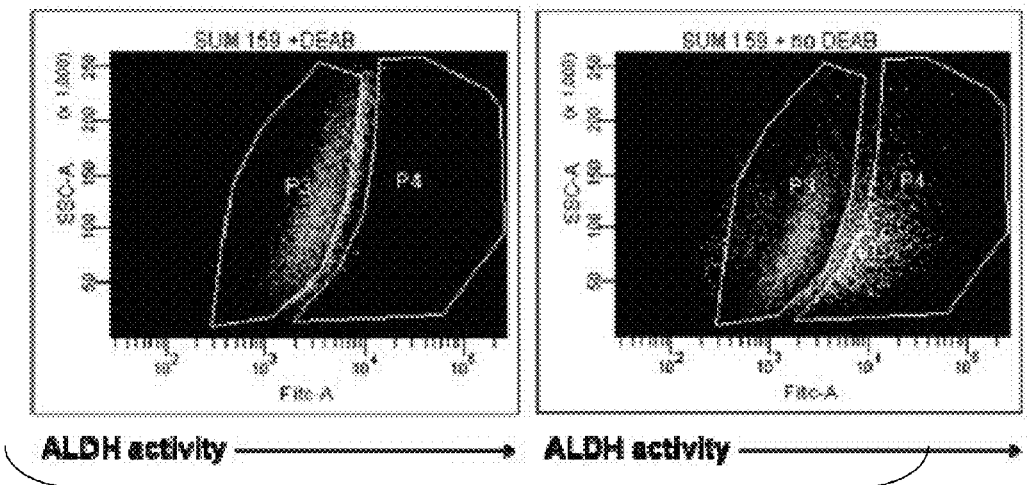
FIGS. 11A-11B. STAT3 phosphorylation of the ALDH$^+$ subpopulation of breast cancer cells is higher than un-separated and the ALDH$^-$ subpopulations.
Figure 11B:
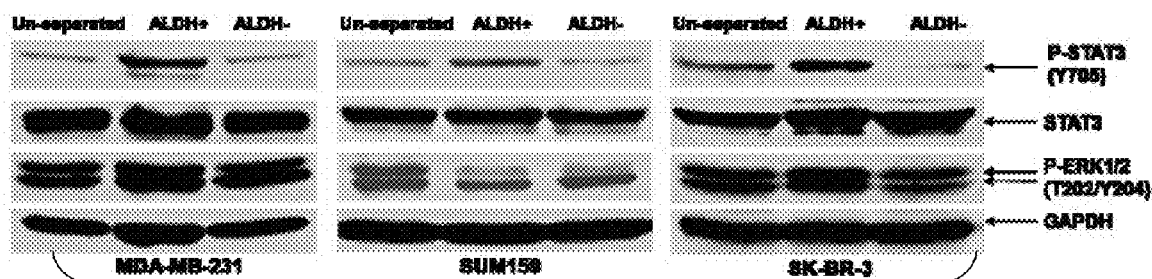
Figure 16A:
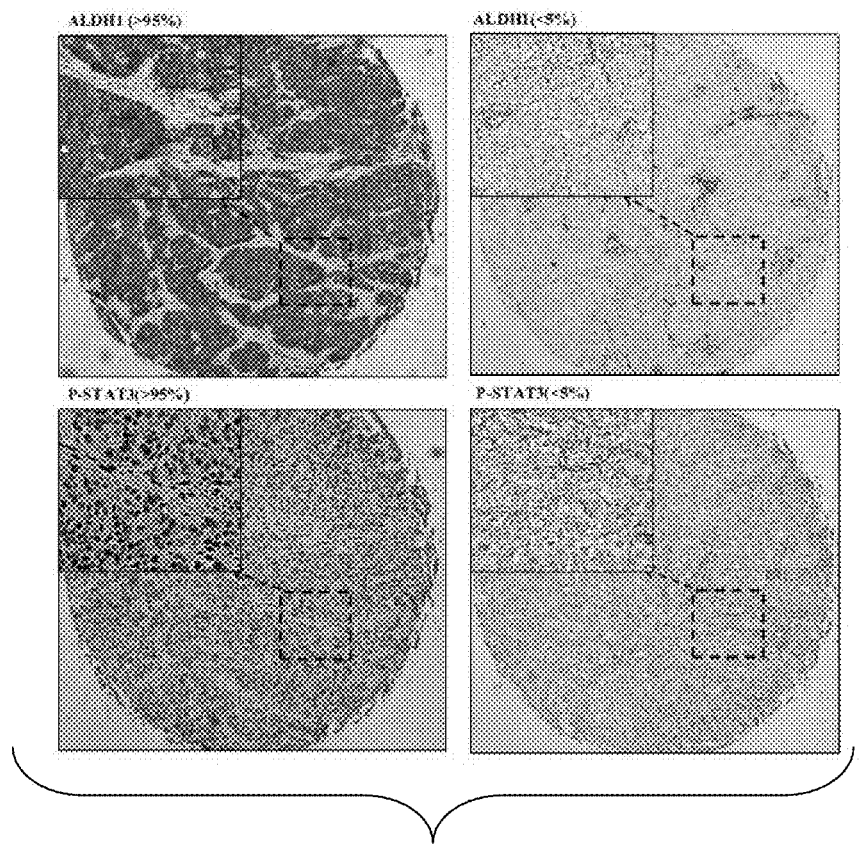
FIGS. 16A-16B. Representative samples of staining of STAT3 phosphorylation of ALDH 1.
Figure 16B:
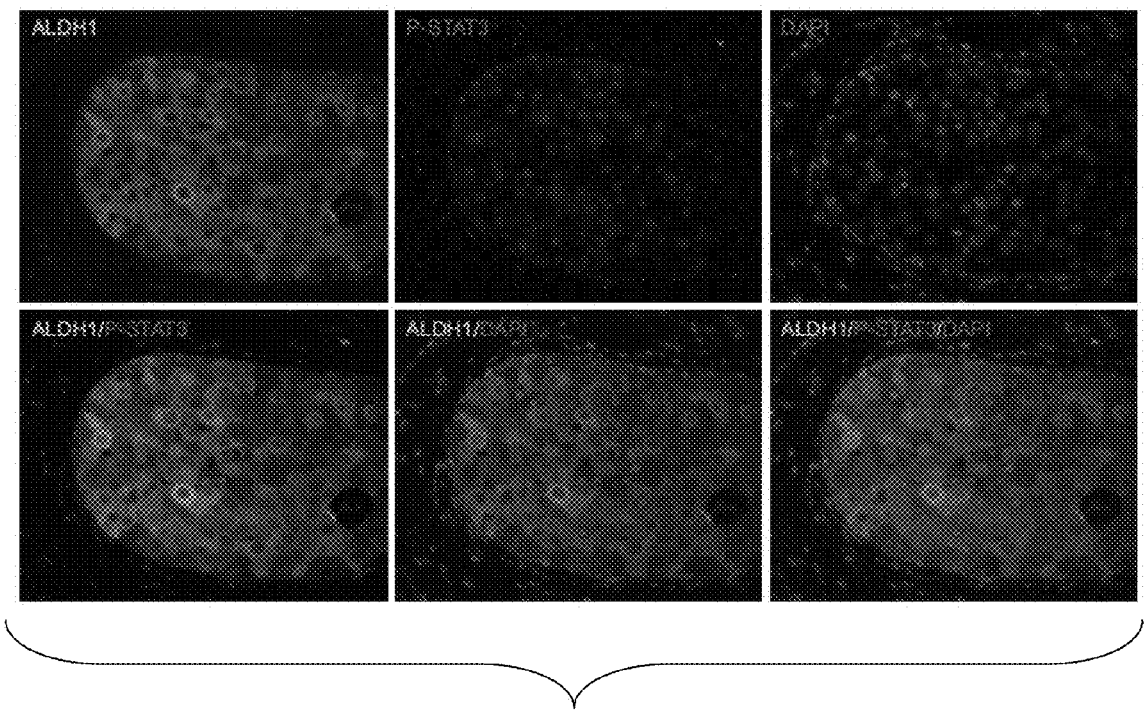

ALDH$^+$ Subpopulation of Breast Cancer Cells (IBC) Expresses High Levels of STAT3 Phosphorylation To determine the expression of phosphorylated STAT3, an activated form of STAT3 in breast cancer initiating cells, the inventors separated the ALDH$^+$ and ALDH$^-$ subpopulations of three breast cancer cell lines, MDA-MB-231, SUM159, and SK-BR-3. A representative example of SUM159 cells is shown in FIG. 11A. It has been demonstrated that the ALDH$^+$ (but not the ALDH) subpopulation in breast cancer cells exhibit cancer stem cell properties in vitro and in the mouse tumor model in vivo. Interestingly, the results showed that the ALDH$^+$ subpopulation of breast cancer cells expresses higher levels of STAT3 phosphorylation (Tyrosine residue 705) compared to un-separated, with the ALDH$^-$ subpopulation being the lowest (FIG. 11B). Phosphorylation at Tyrosine residue 705 (Y705) is important for activating STAT3. ERK1/2 phosphorylation at threonine 202/tyrosine 204 (T202/Y204) is not consistently high in the ALDH$^+$ subpopulation. These results show that ERK likely does not play a key role in breast cancer initiating cells, at least in these three breast cancer cell lines. In contrast, the STAT3 pathway is activated in the ALDH$^+$ subpopulation and appears to be more important in breast cancer initiating cells. The inventors also examined the STAT3 phosphorylation and ALDH1 protein expression in human breast cancer tissues using Tissue microarray slides. The inventors observed that there is a significant association (P<0.01) between the nuclear staining of STAT3 phosphorylation and staining of ALDH1. The representative examples of staining of STAT3 phosphorylation and staining of ALDH1 were shown in FIGS. 16A and 16B. The results from breast cancer patients further support the data in breast cancer cell lines that the elevate levels of STAT3 phosphorylation is expressed in breast cancer initiating cells. This is the first report to demonstrate that breast cancer initiating cells express elevated levels of STAT3 phosphorylation (Table 4), which indicates that constitutive STAT3 signaling may be a novel therapeutic target in breast cancer initiating cells.

TABLE 4

The association of P-STAT3 (Y705) with the expression of ALDH1 in breast carcinoma.

| | n | ALDH1 Positive Number | ALDH1 Positive % | P-STAT3 Positive Number | P-STAT3 Positive % | ALDH1/P-STAT3 Both Positive Number | ALDH1/P-STAT3 Both Positive % | ALDH1/P-STAT3 Both Negative Number | ALDH1/P-STAT3 Both Negative % | $\chi^2$ | P* |
|---|---|---|---|---|---|---|---|---|---|---|---|
| Breast Carcinoma | 95 | 23 | 24 | 33 | 35 | 18 | 18 | 57 | 60 | 25.358 | 4.8e−7 |

LLL12, a Small Molecular STAT3 Inhibitor, Selectively Inhibits STAT3 Phosphorylation, STAT3 Downstream Targets, and Induces Apoptosis in Breast Cancer Cells.

Figure 17:
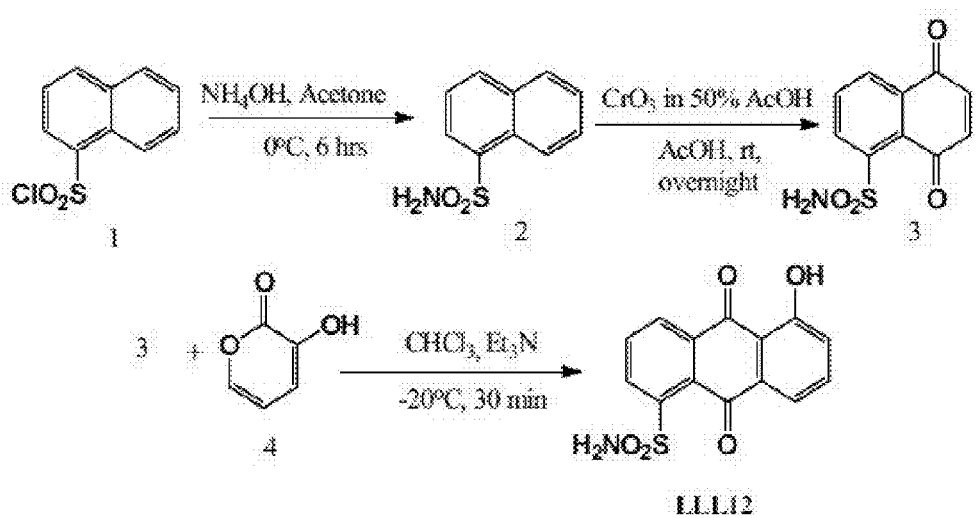
FIG. 17. LLL12 synthesis and compound.
Figure 18:
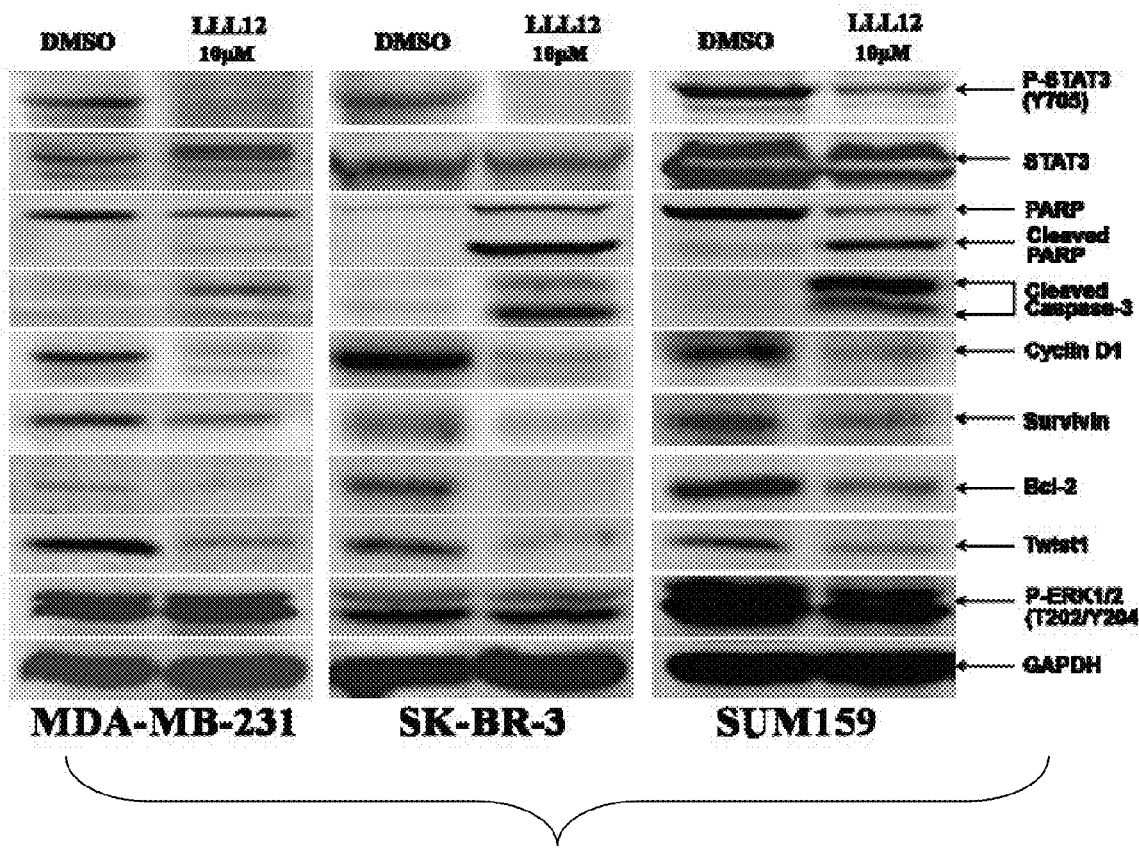
FIG. 18. LLL12 inhibits STAT3 phosphorylation in unseparated MDA-MB-231, SK-BR-3, and SUM159 breast cancer cell lines.
Figure 19A:
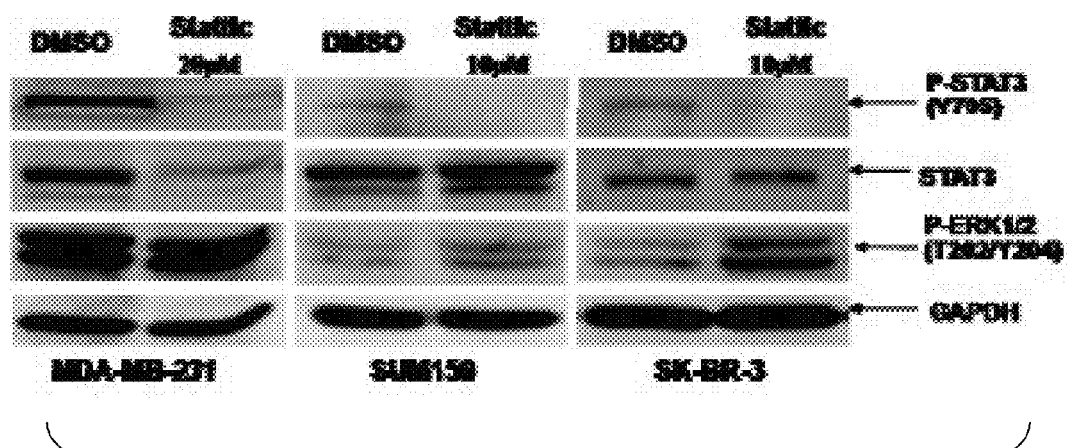
FIG. 19. Stattic reduces STAT3 phosphorylation in ALDH+ cells.
Figure 19A:
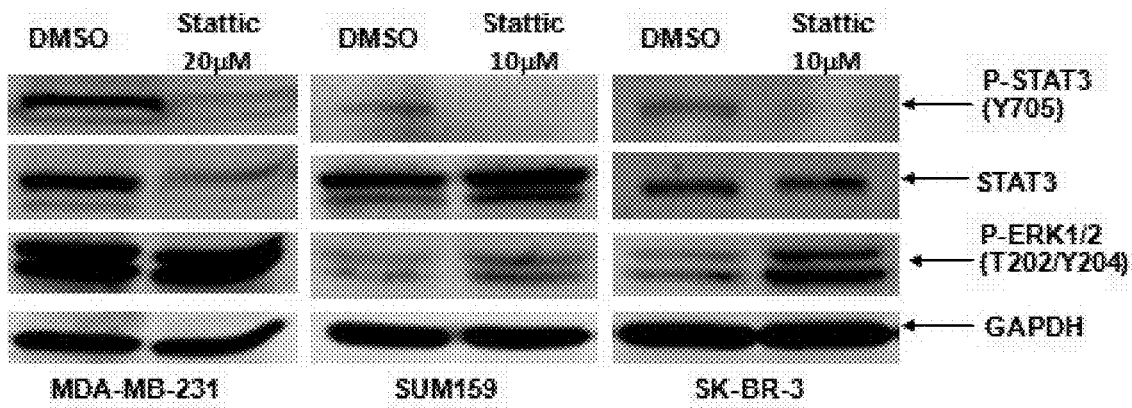
Figure 19B:
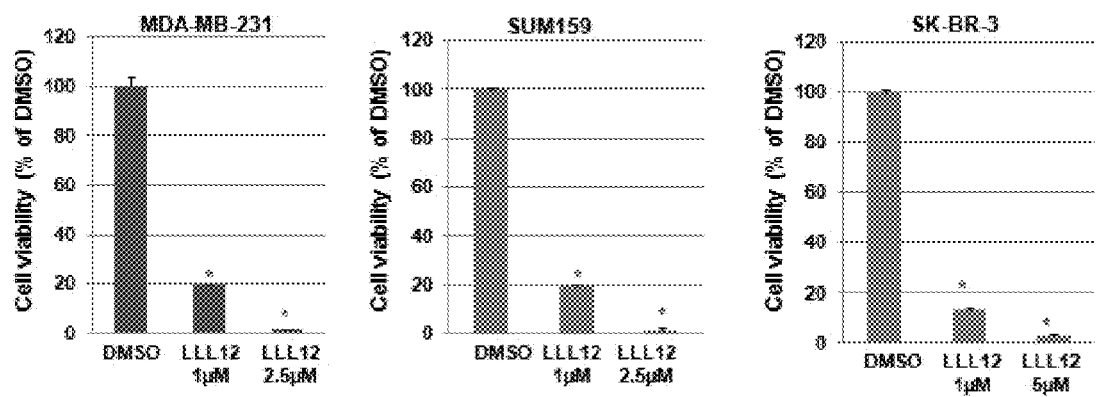
Figure 19C:
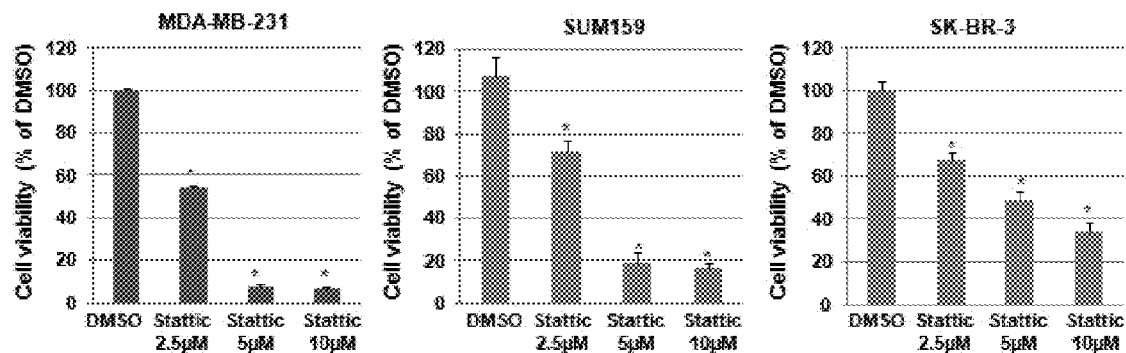
Figure 19D:
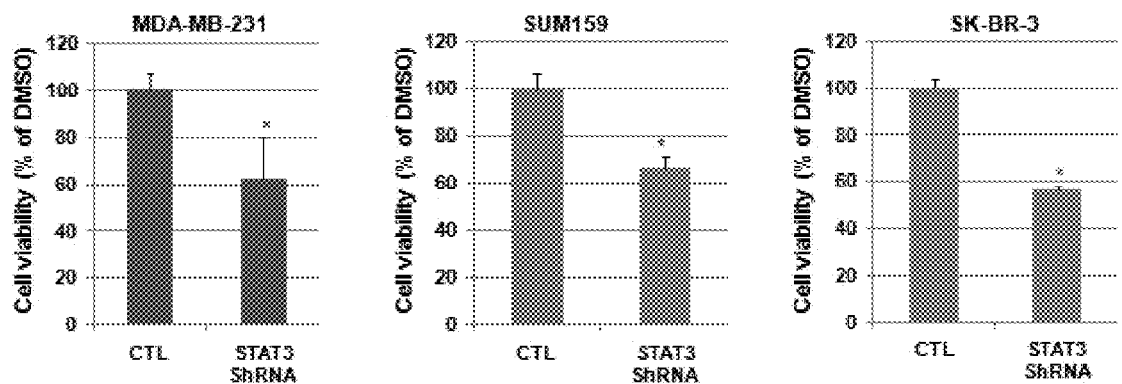

To confirm the important role of STAT3 in breast cancer initiating cells, the STAT3 inhibitor, LLL12 (FIG. 17), which is a novel analog of a previously reported STAT3 inhibitor LLL3, was used to target STAT3 in breast cancer initiating cells. LLL12 contacts STAT3 SH2 domain at Y705 and partially binds to the side pocket close to Y705 in a computer docking model via AutoDock. To confirm the inhibition of STAT3 by LLL12, the inventors examined the inhibition of STAT3 phosphorylation in three independent breast cancer cell lines. The results demonstrated that LLL12 inhibited STAT3 phosphorylation in un-separated MDA-MB-231, SK-BR-3, and SUM159 breast cancer cell lines (FIG. 18). However, LLL12 did not inhibit the phosphorylation of ERK, indicating that the inhibition was specific to STAT3. The inventors further examined whether LLL12 may inhibit other human kinase activity besides inhibiting STAT3 which may partially account for the inhibition of breast cancer stem cell viability. LLL12 exhibits little inhibition (IC50 are greater than 100 μM) on tyrosine kinases, Fes, JAK2, Bmx, c-SRC, PYK2, Syk, Fyn, and Yes containing SH2 domain or both SH2 and SH3 domains (Table 5). LLL12 also exhibits little inhibition (IC50 are 77.94 μM or greater) to other protein kinases that are involved in cell proliferation and survival including AKT1, c-Raf, EGFR, ErB2/HER2, Met, mTOR, PDK1, PI3K, and others (Table 5). To the knowledge, this may be the first STAT3 inhibitor that has been tested against many human protein and lipid kinases for its selectivity. LLL12 also inhibited STAT3 but not STAT1 DNA binding activity. These results strongly support the specificity of LLL12 to inhibit STAT3 and the ability of LLL12 to inhibit breast cancer initiating cells is due to the inhibition of STAT3. Furthermore, LLL12 also reduced the expression of STAT3 downstream genes, such as Cyclin D1, Survivin, Bcl-2 and Twist1, and subsequently induced apoptosis of these human breast cancer cells as indicated by an increase in levels of cleaved PARP and Caspase-3 (FIG. 18).

TABLE 5

The effect of LLL12 on human protein and lipid kinases

|  | Protein Kinases | IC50 (μM) | Protein Kinases | IC50 (μM) |
|---|---|---|---|---|
| Tyrosine kinases contain S H2 Domain | Fes | >100 | Pyk2 | >100 |
|  | JAK2 | >100 | Syk | >100 |
| Tyrosine kinases contain S H2 and S H3 Domains | Bmx | >100 | Fyn | >100 |
|  | c-SRC | >100 | Yes | >100 |
| Other human protein or lipid kinases | AKT1 | >100 | mTOR | >100 |
|  | CDK4/CyclinD1 | 77.94 | P38 | >100 |
|  | CDK6/CyclinD1 | >100 | PAK1 | >100 |
|  | CHK1 | >100 | PDK1 | >100 |
|  | C-Kit | >100 | P13K (P110a/85a) | >100 |
|  | C-RAF | >100 | P13K (P110b/85a) | >100 |
|  | EGFR | >100 | PKC-b | >100 |
|  | Erb B2/H ER2 | >100 | TAK1 | >100 |
|  | Met | >100 | VEGFR1 | >100 |

LLL12 Inhibits STAT3 Phosphorylation and STAT3 Downstream Targets in ALDH+ Cells.

Figure 2A:
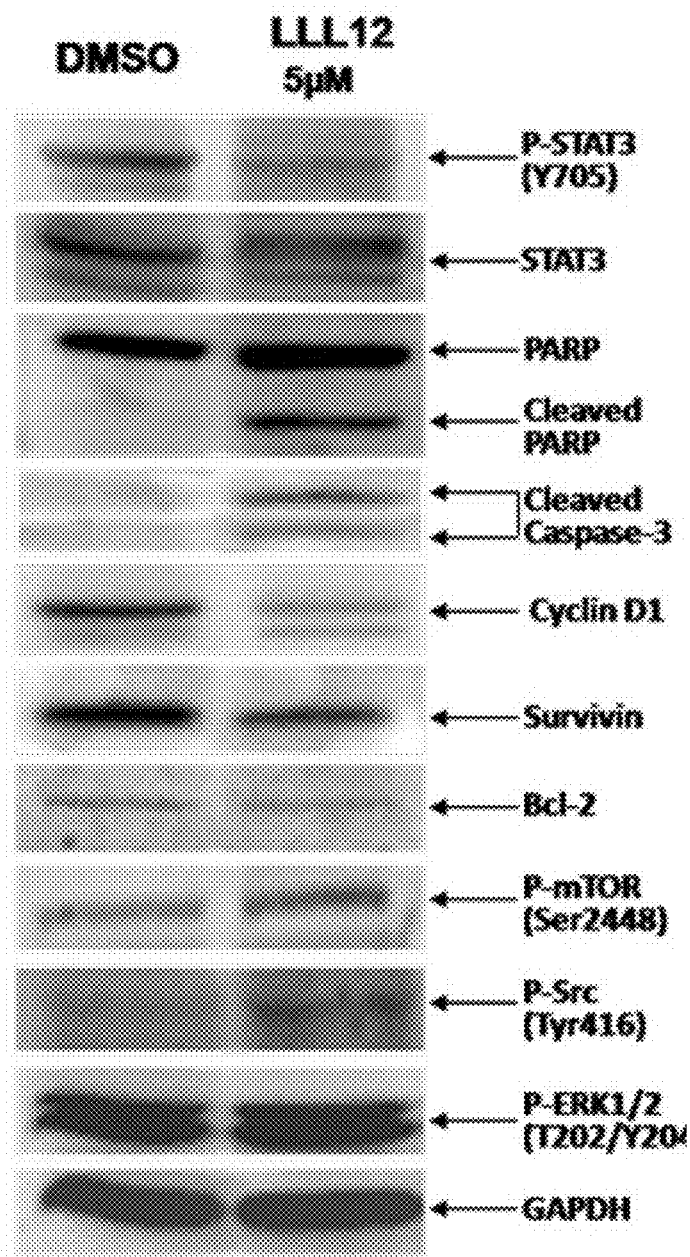
FIGS. 2A-2E. Western Blot analysis of cells treated with LLL12. Cancer cell lines expressing constitutively active STAT3, (FIG. 2A) MDA-MB-231, (FIG. 2B) SK-BR-3, (FIG. 2C) HPAC, (FIG. 2D) U87, exhibit a decrease in the levels of expression of STAT3 phosphorylation after treatment with LLL12. Downstream targets of STAT3, cyclin D1, Bcl-2, and survivin, were inhibited. Apoptosis is also indicated by the induction of cleaved PARP and caspase-3. Normal cell lines which do not express elevated levels of STAT3 phosphorylation, (FIG. 2E) Human Pancreatic Duct Epithelial cells (HPDE), Human Mammary Epithelial Cells (HMEC), Human Hepatocytes (HH), and normal human lung fibroblasts (WI-38), did not exhibit an induction of cleaved PARP or caspase-3 following treatment with LLL12.
Figure 2B:
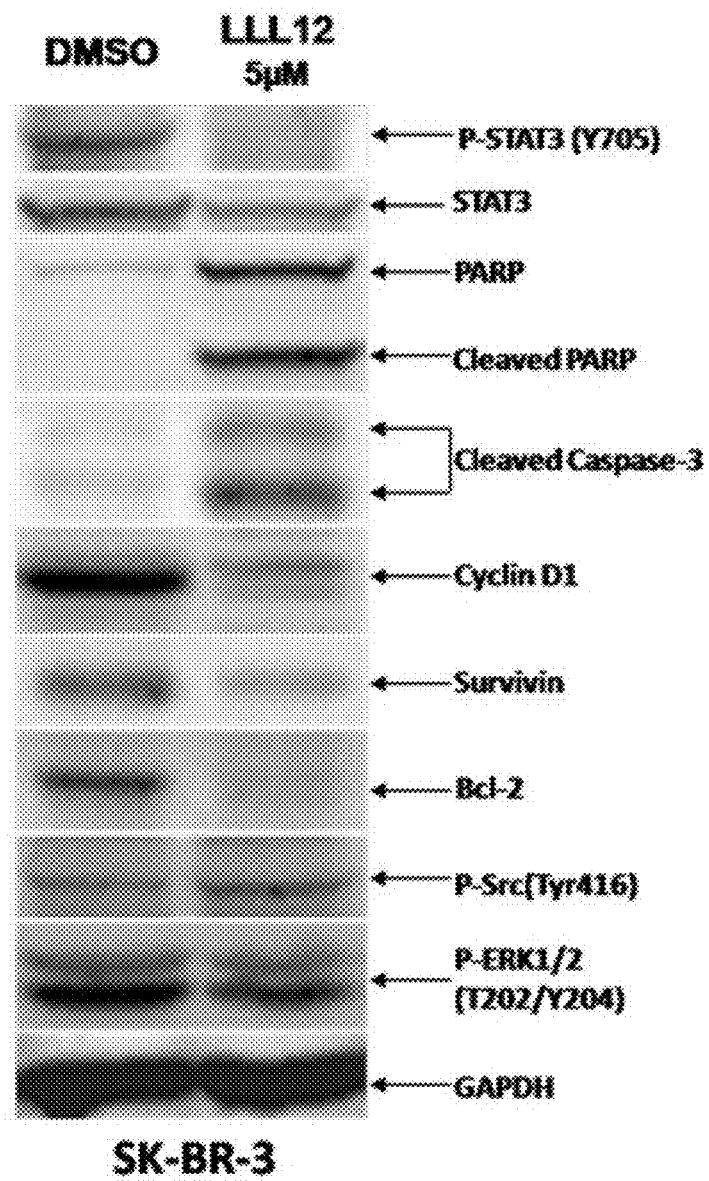
Figure 2C:
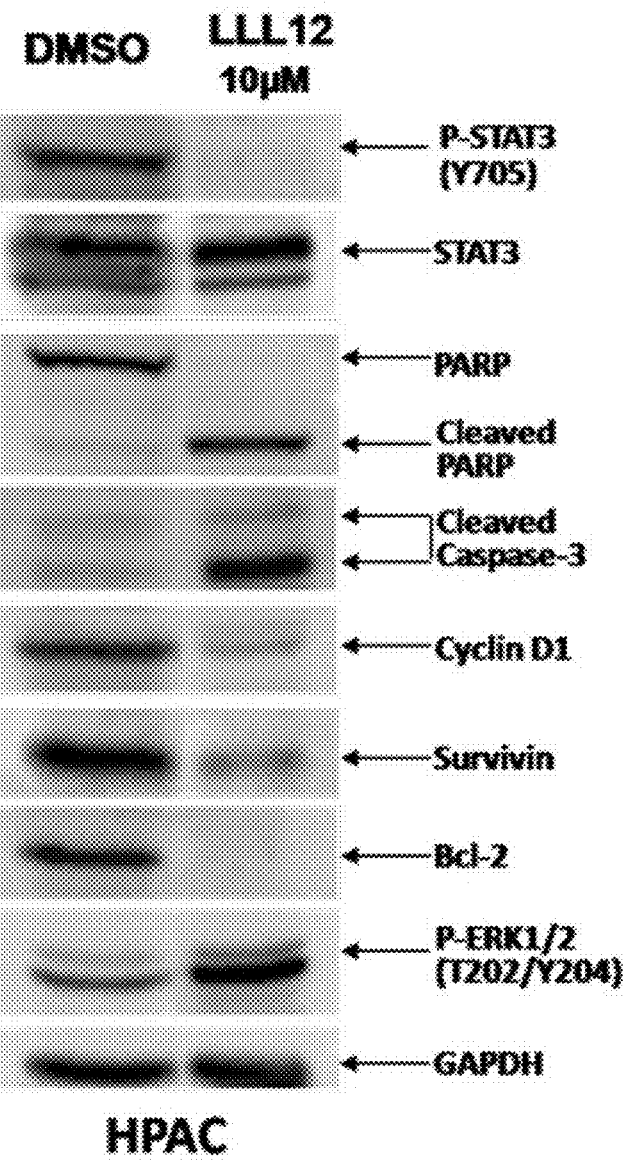
Figure 2D:
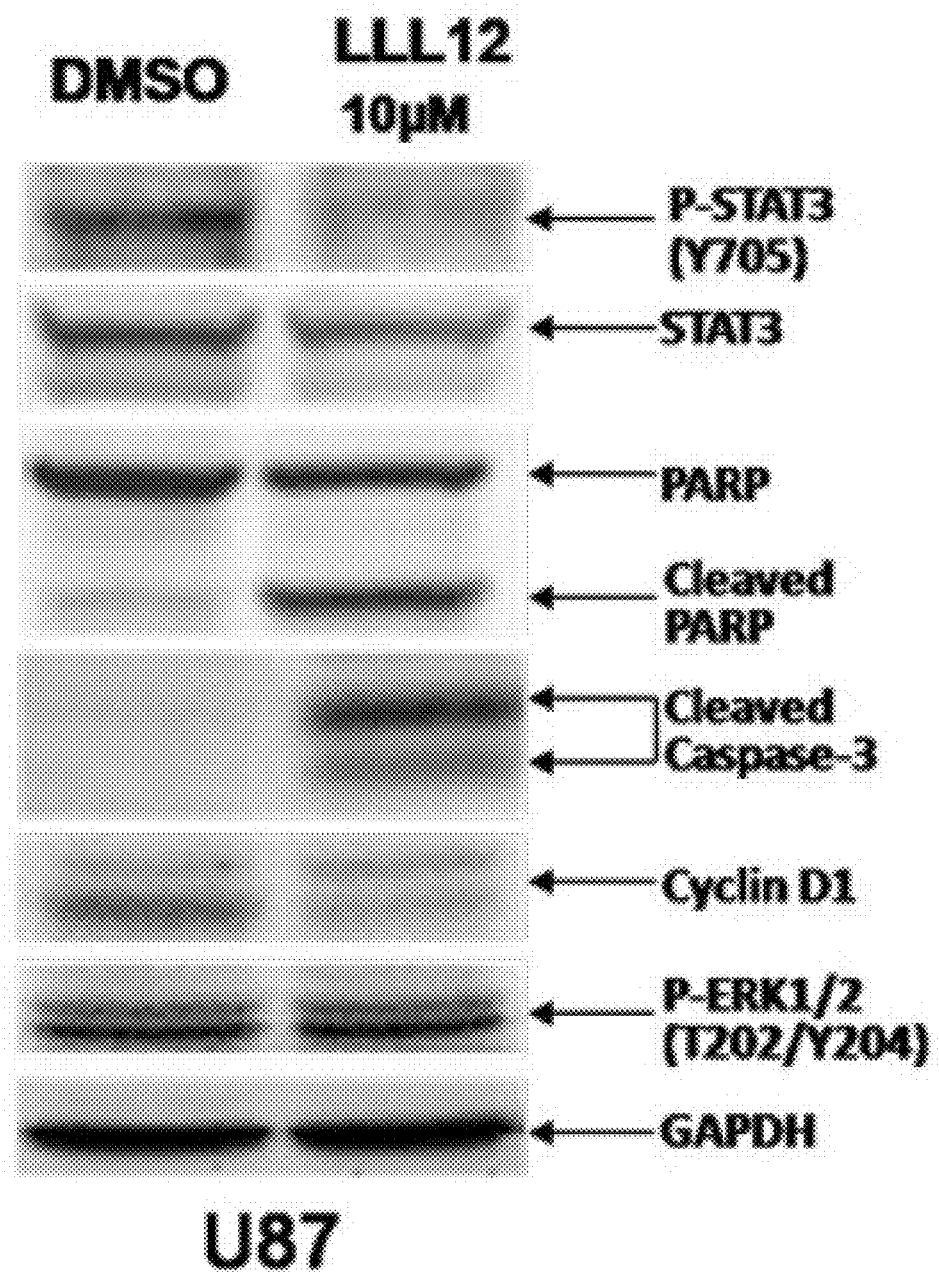
Figure 2E:
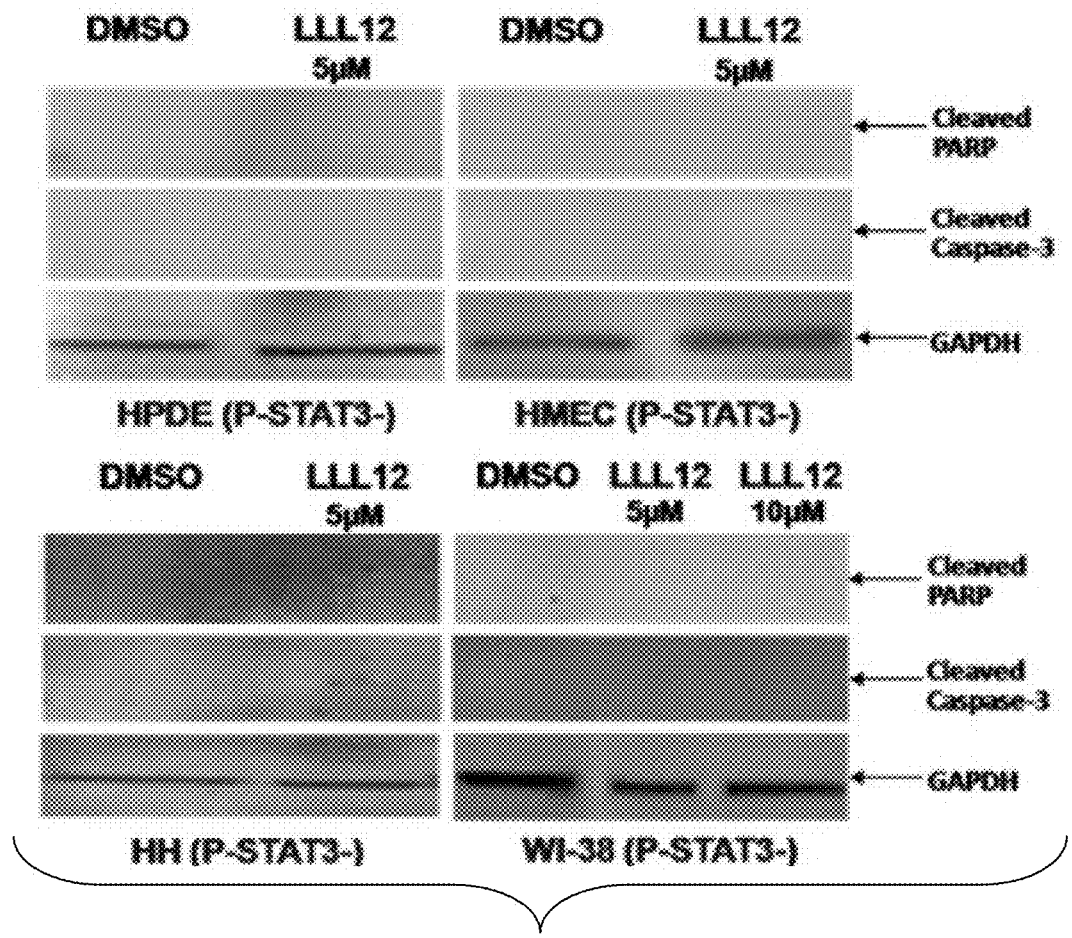
Figure 12A:
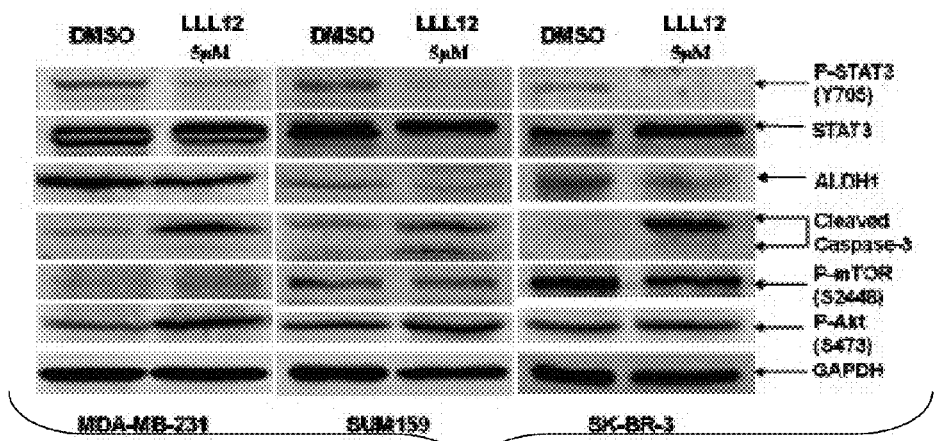
FIGS. 12A-12C.
Figure 12B:
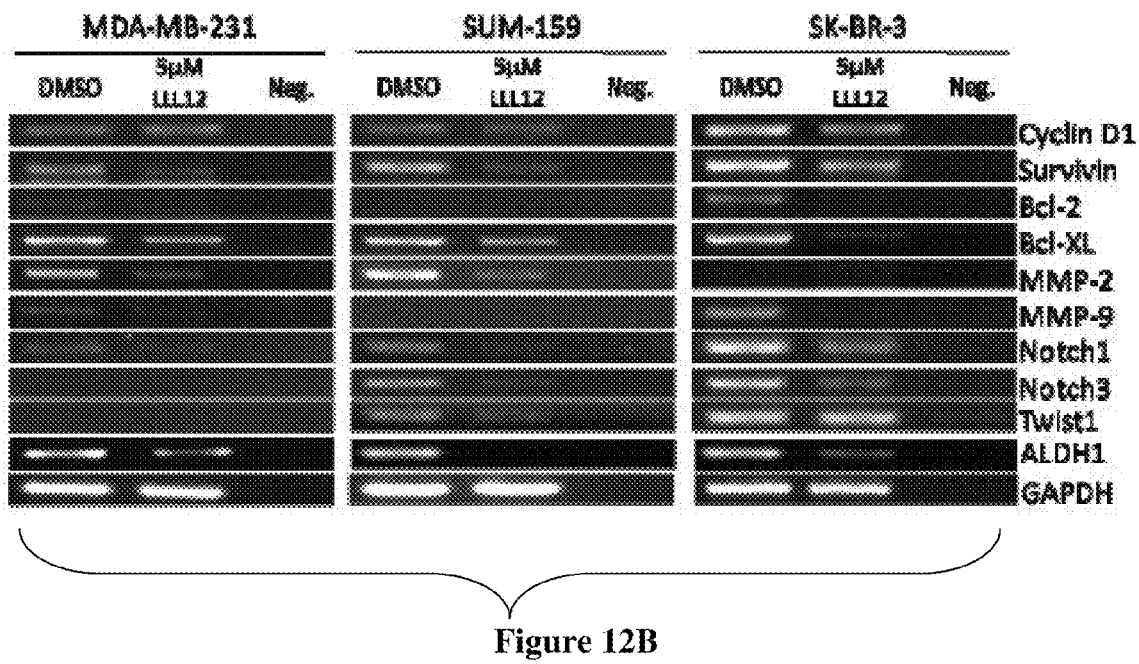
Figure 12C:
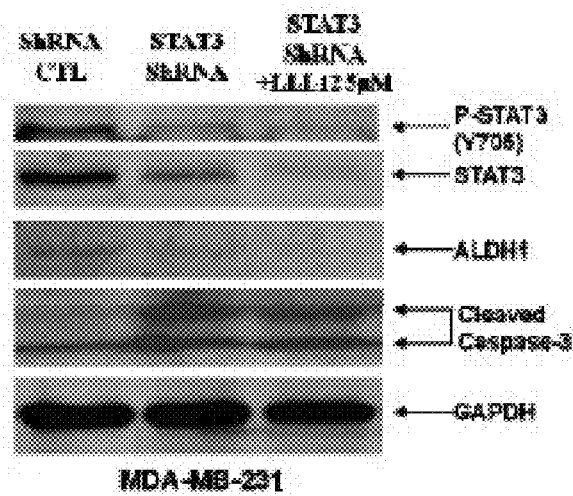

The inventors next examined the effect of LLL12 on breast cancer initiating cells and the results demonstrated that LLL12 inhibits STAT3 phosphorylation and induces cleaved caspase-3 in the ALDH+ subpopulation of MDA-MB-231, SUM159, and SK-BR-3 (FIG. 2A). The inhibition of STAT3 by LLL12 also down-regulates the expression of many known STAT3-regulated genes in breast cancer initiating cells related to cancer cell proliferation, survival, and angiogenesis, such as Cyclin D1, surviving, Bcl-2, Bcl-XL (9), MMP-2, and MMP-9 (FIG. 12B). Furthermore, LLL12 inhibits Twist1, Notch-1, and Notch-3 expression in breast cancer initiating cells, which have recently been reported as putative STAT3 or Interleukin-6 target genes (FIG. 12B). Twist1 has been shown to play an important role in the epithelial to mesenchymal transition and malignant transformation. The Notch signaling pathway is known to be essential for normal stem cell self-renewal and differentiation in a variety of tissues, and is involved in human cancer stem cells' self-renewal capacity and tumorigenicity. These results indicate the LLL12 is also potent in terms of inhibiting STAT3 phosphorylation, down-regulating STAT3-dowmstream genes, and inducing apoptosis in these breast cancer initiating cells. The inventors also observed that STAT3 ShRNA inhibits STAT3 phosphorylation and induces cleaved caspase-3 in the absence or presence of LLL12 (FIG. 12C). In addition, Stattic also reduces STAT3 phosphorylation in ALDH+ cells (Supplemental FIG. 4).

STAT3 Inhibitors, LLL12 and Stattic can Reduce ALDH+ Subpopulation of Breast Cancer Cells.

Figure 13A:
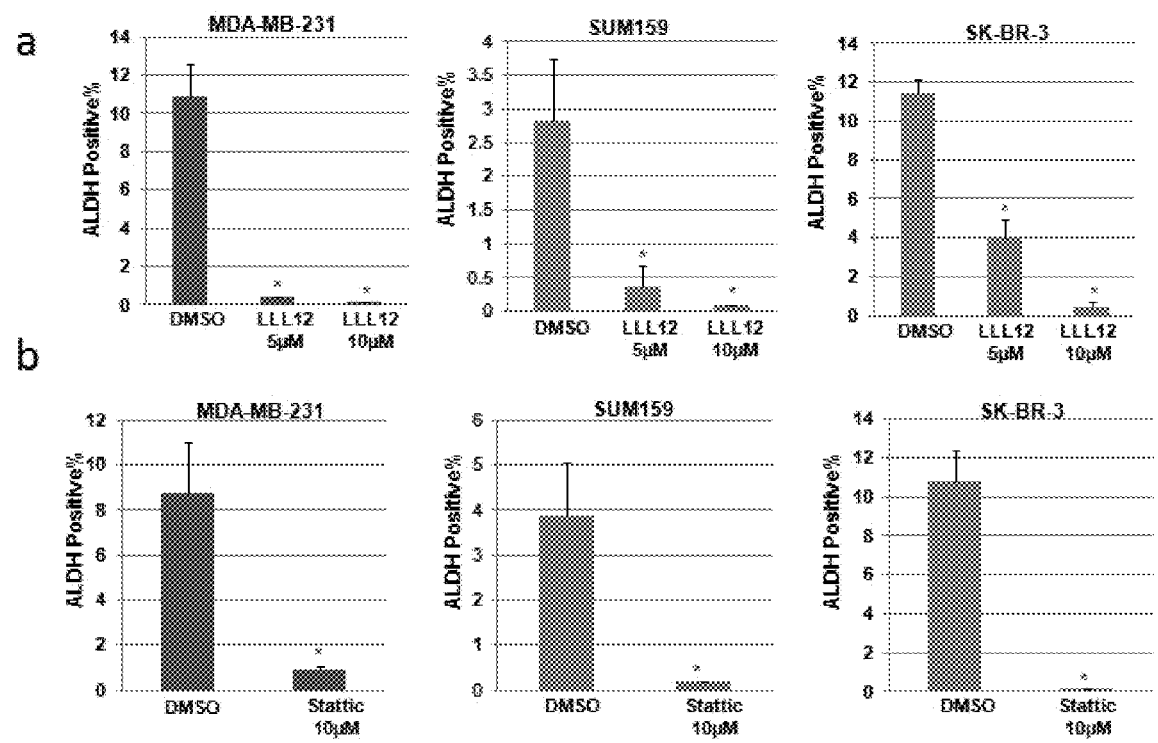
FIGS. 13A-13D. LLL12 (FIG. 13A) and Stattic (FIG. 13B) reduced the ALDH$^+$ subpopulation of MDA-MB-231, SUM159, and SK-BR-3 breast cancer cells. Statistically significant reduction of LLL12-treated relative to the DMSO is designated by an asterisk (P<0.05). LLL12 (FIG. 13C), Stattic (FIG. 13D).
Figure 13B:
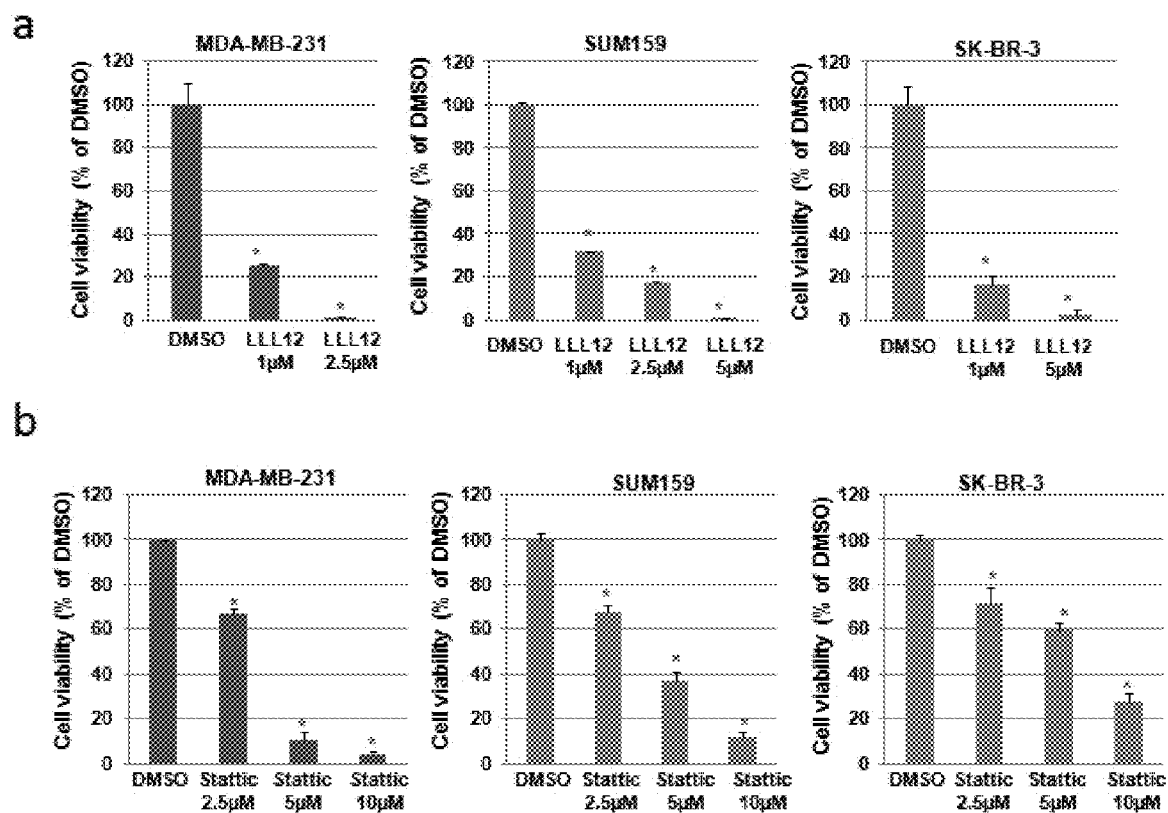

Cancer stem cells are resistant to current chemotherapy and radiation regimens available for breast cancer. To examine whether LLL12 might eliminate the ALDH+ subpopulation, the inventors treated cancer cells and sorted for the percentage of ALDH+ subpopulation. If breast cancer initiating cells are resistant to LLL12, the ALDH+ subpopulation should increase. However, the results showed that LLL12 could decrease the ALDH+ subpopulation in MDA-MB-231, SUM159, and SK-BR3 cancer cells (FIG. 13A), suggesting that this subpopulation of breast cancer initiating cells is sensitive to LLL12-mediated inhibition. The inventors found that 10 μM of Stattic, another previously reported STAT3 inhibitor, also decreased the percentage of ALDH+ subpopulation (FIG. 13B). The results confirm that the STAT3 pathway plays a central role in the maintenance of the ALDH+ subpopulation in breast cancer cells.

ALDH+ Cells are Sensitive to the Inhibition by STAT3 Inhibitors and STAT3 ShRNA.

Figure 13C:
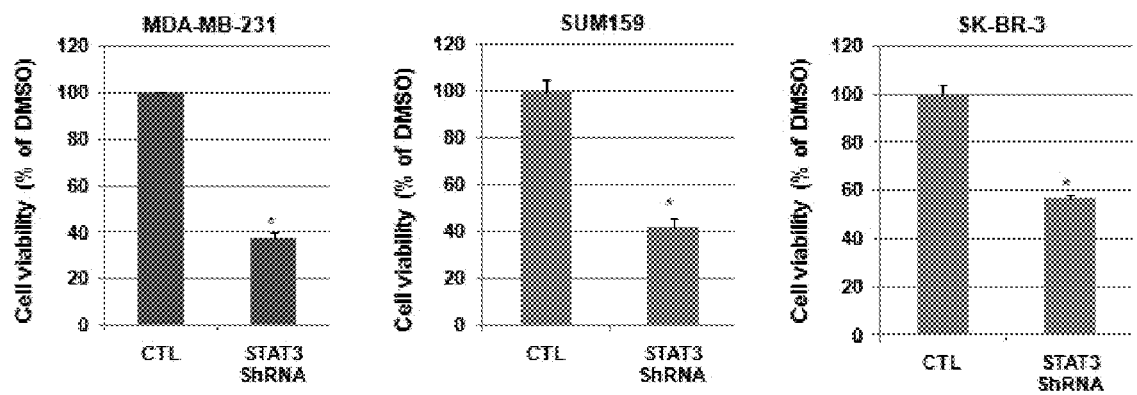
Figure 13D:
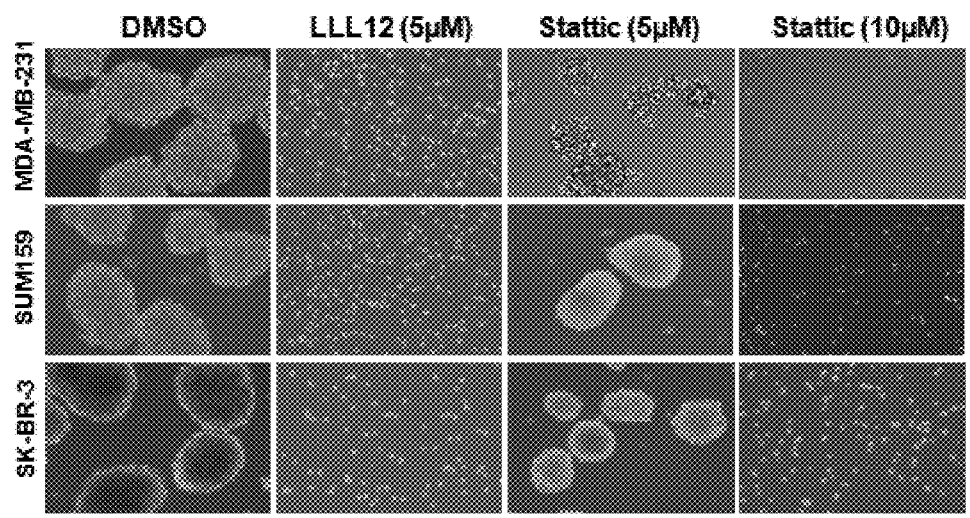

In addition, the inventors observed that LLL12 (FIG. 13C) and Stattic (FIG. 3D) can inhibit cell viability of the ALDH+ subpopulation from MDA-MB-231, SUM159, and SK-BR3 cells, although LLL12 is more potent than Stattic in terms of inhibiting breast cancer initiating cell viability. Also, STAT3 ShRNA reduced cell viability of the ALDH+ cells (FIG. 13E). These results support that breast cancer stem cells are sensitive to STAT3 inhibitors. Furthermore, mammary tumor stem and progenitor cells were able to survive and proliferate in anchorage-independent conditions and form floating spherical colonies that were termed as "tumorspheres". The results also demonstrated that LLL12 and Stattic can inhibit tumorsphere forming capacity in the ALDH+ subpopulation of SK-BR-3, MDA-MB-231, and SUM159 (FIG. 13F); again, LLL12 shows more potent activity than Stattic in inhibiting tumorsphere formation in the comparisons. Consistently, in the computer model for binding to STAT3 SH2 domain, LLL12 (−7.8 Kcal/mol) exhibits higher predictive binding affinity 57.8-fold stronger than Stattic (−5.6 Kcal/mol). The possible effects of ALDH− cells by STAT3 inhibitors and STAT3 ShRNA was also examined. There are also inhibitory effects ALDH− cells by LLL12, Stattic and STAT3 ShRNA (FIG. 19). This may be expected because ALDH− cells still express certain levels of STAT3 phosphorylation (FIG. 11B).

LLL12 Suppresses Tumor Growth of Breast Cancer Initiating Cells in Mouse Tumor Xenograft and Orthotopic Model In Vivo.

Figure 14A:
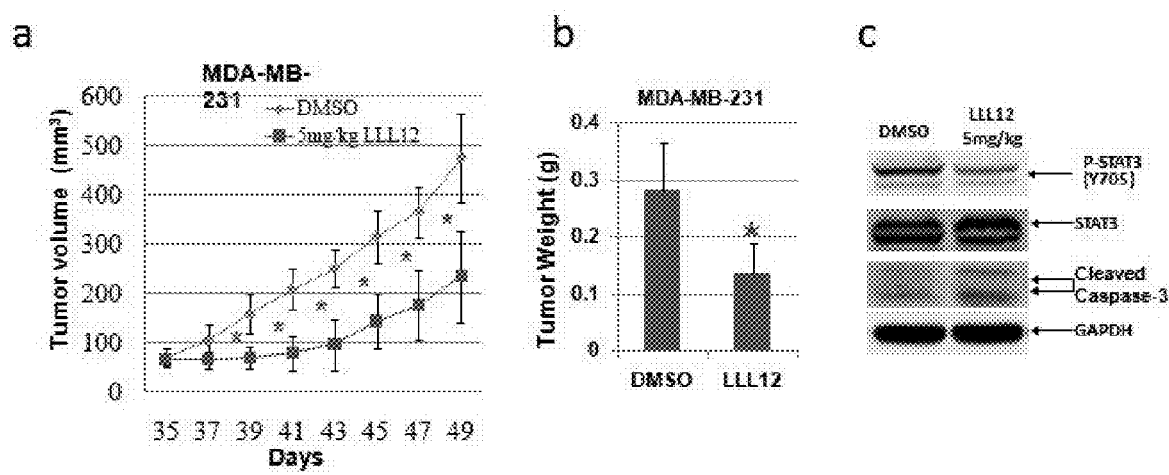
FIGS. 14A-14B. LLL12 suppresses tumor growth in mouse xenografts (FIG. 14A to FIG. 14B). Reduction of tumor volume (FIG. 14A) and tumor weight (FIG. 14B) in all six LLL12-treated mice compared to DMSO vehicle group (*P<0.05).
Figure 14B:
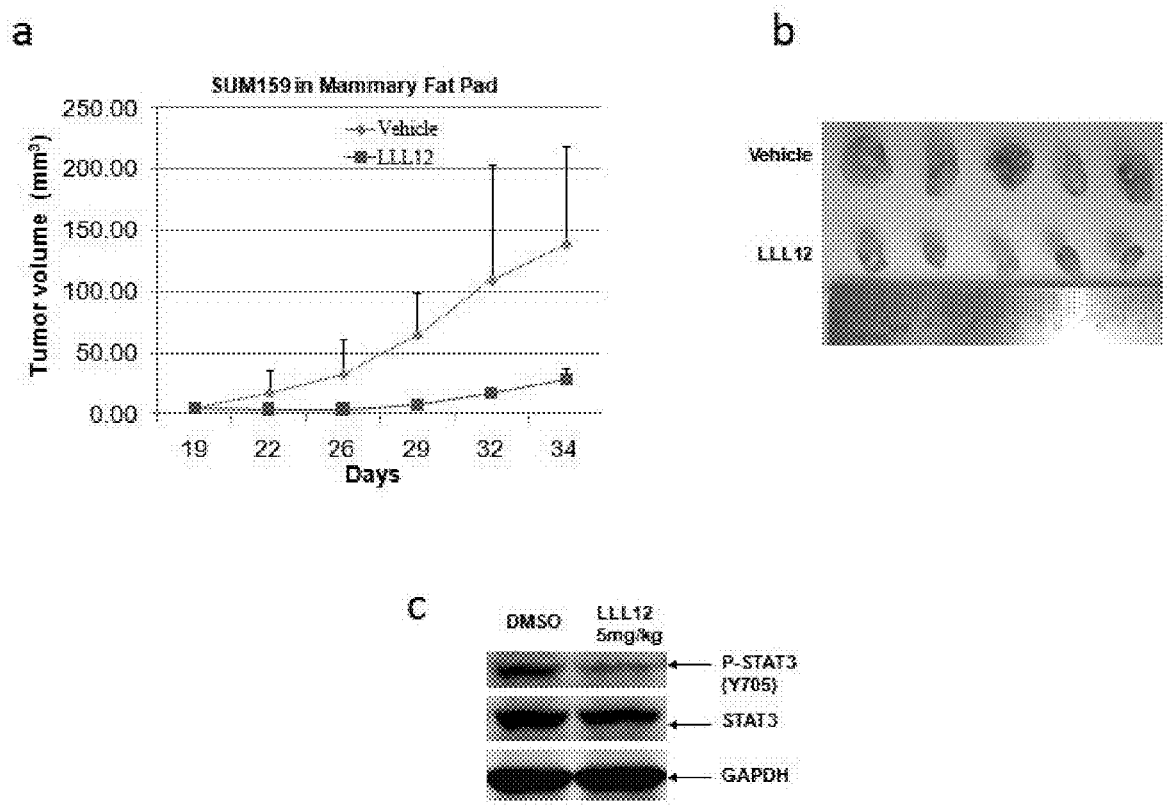

To determine whether LLL12 may have a therapeutic potential for clinical breast carcinoma treatment, the inventors further tested LLL12 against breast cancer initiating cells isolated from the MDA-MB-231 and SUM159 breast cancer cells in NOD/SCID mice xenograft and mammary fat pad models respectively in vivo. The results from the administration of LLL12 showed that LLL12 significantly suppresses (P<0.01) tumor volume (FIG. 14A) and tumor weight (FIG. 14B), and STAT3 phosphorylation (FIG. 14C) of MDA-MB-231 breast cancer initiating cells in the xenograft mouse model. The similar results were observed in the treatment of LLL12 showing that significantly suppresses (P<0.01) of tumor volume (FIG. 14D) and tumor mass (FIG. 14E), and STAT3 phosphorylation (FIG. 14F) of SUM159 breast cancer initiating cells in the mammary fat pad mouse model. These results demonstrated that LLL12 is potent in suppressing tumor growth from the breast cancer initiating cells in vivo.

ALDH+/CD44+/CD24− Subpopulation of Breast Cancer Cells Expresses High Levels of STAT3 Phosphorylation and is Sensitive to LLL12 Inhibition.

Figure 15A:
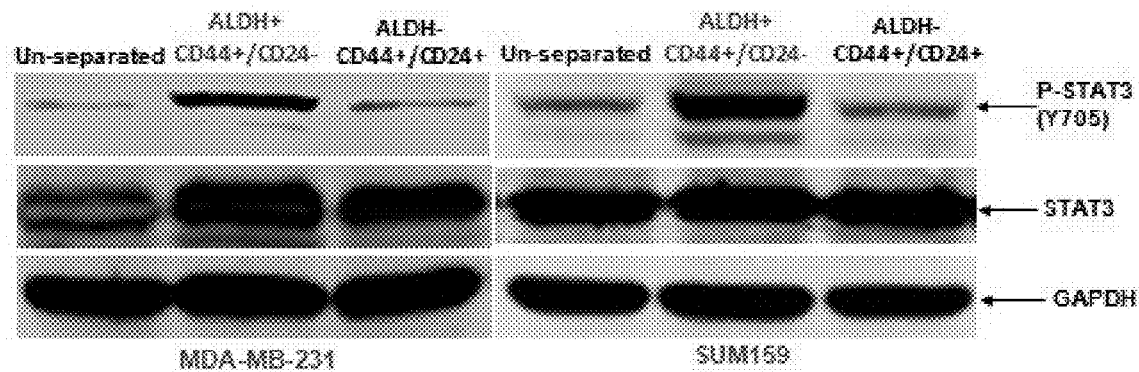
Figure 15B:
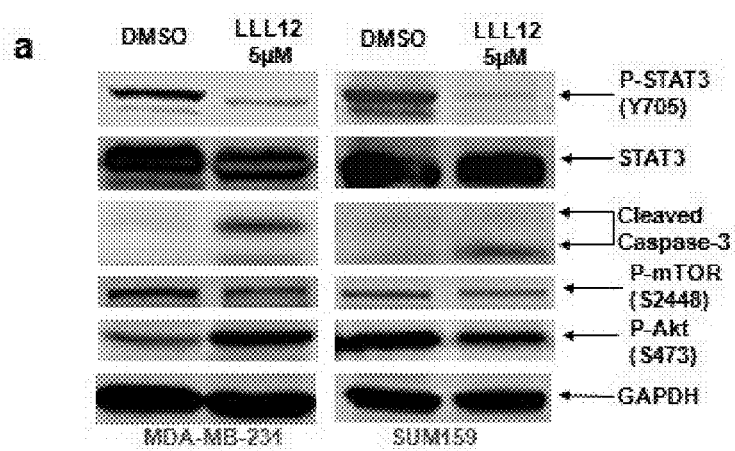
Figure 15B:
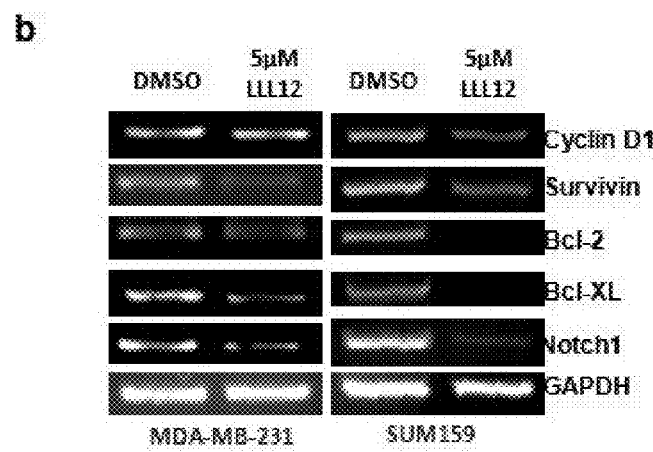
Figure 15D:
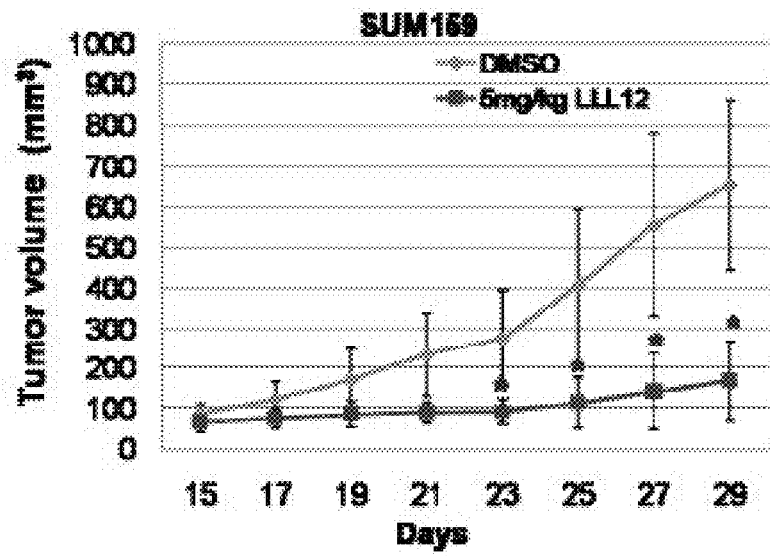
Figure 20:
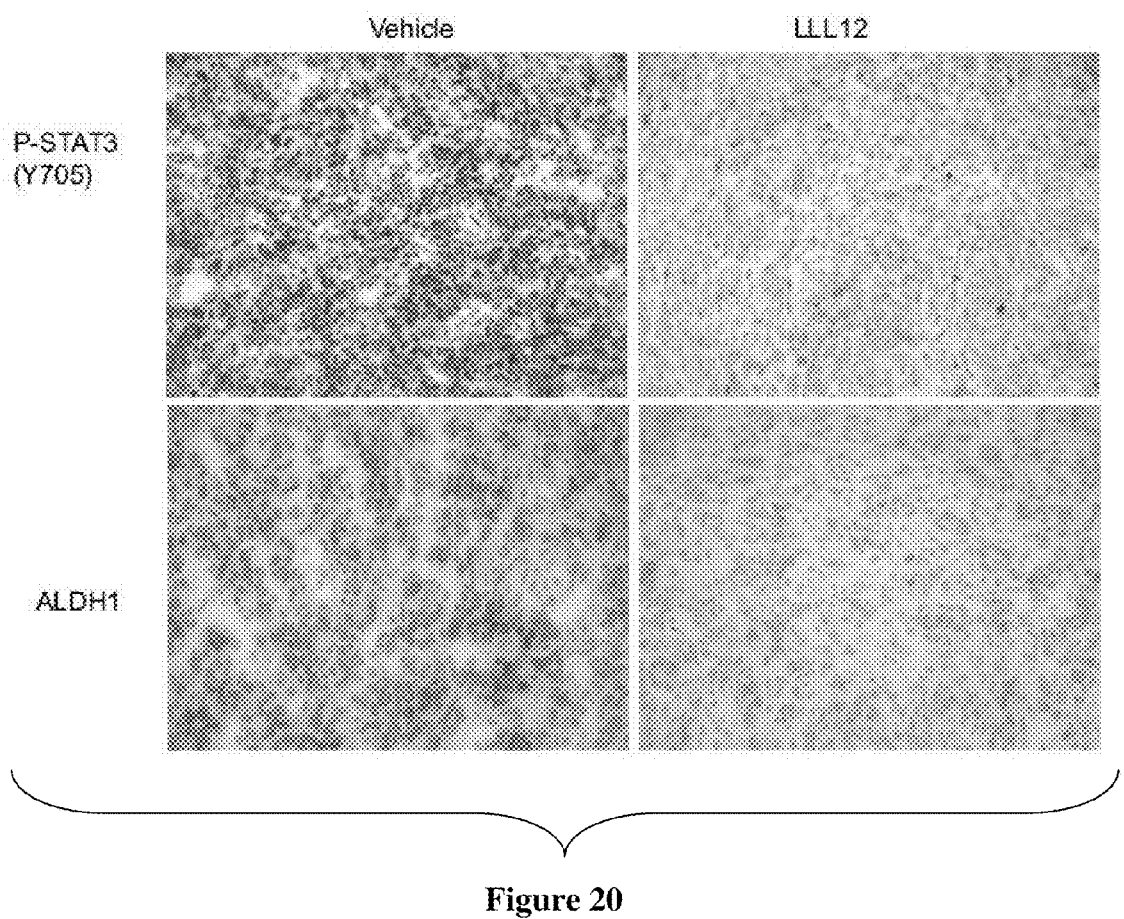
FIG. 20. Vehicle versus LLL12 on P-STAT3 (Y705) and ALDH1 in vivo.

Breast cancer cells that express the cell surface molecule CD44 (CD44+) but lack or have low expression of CD24 (CD24$^{low/−}$) have also been described as cancer stem cells. The inventors therefore isolated ALDH+/CD44+/CD24− cells to further enrich the stem cell population (FIG. 20). Again, the results showed that the ALDH+/CD44+/CD24− subpopulation of MDA-MB-231 and SUM159 breast cancer cells expresses higher levels of STAT3 phosphorylation compared to the un-separated and ALDH−/CD44+/CD24+ subpopulations (FIG. 15A). The inventors next examined the effect of LLL12 on breast cancer initiating cells and the results demonstrated that LLL12 inhibits STAT3 phosphorylation and induces cleaved caspase-3 in the ALDH+/CD44+/CD44+/CD24− subpopulation of MDA-MB-231 and SUM159 (FIG. 15B). There is slightly reduced of mTOR phosphorylation in both cell lines and slightly reduced of AKT phosphorylation in SUM159 but increased in MDA-MB231 cells (FIG. 15B). The inhibition of STAT3 by LLL12 also down-regulates the expression of known STAT3-regulated genes in breast cancer initiating cells such as Cyclin D1, survivin, Bcl-2, Bcl-XL and IL-6 regulated gene, Notch1 (FIG. 15C). In addition, the inventors observed that LLL12 inhibited cell viability in the ALDH$^+$/CD44$^+$/CD24$^+$ subpopulation of MDA-MB-231 and SUM159 breast cancer cells (FIG. 15D). Furthermore, LLL12 inhibits tumorsphere forming capacity in the ALDH$^+$/CD44$^+$/CD24$^-$ subpopulation of MDA-MB-231 and SUM159 breast cancer cells (FIG. 15E). To determine whether LLL12 may have a therapeutic potential on ALDH$^+$/CD44$^+$/CD24– cells, the inventors further tested LLL12 against breast cancer initiating cells isolated from the SUM159 cancer cells in nude mice xenograft model in vivo. The results from the administration of LLL12 showed that LLL12 significantly suppresses ($P<0.05$) tumor volume (FIG. 15F) of SUM159 breast cancer initiating cells in xenograft mouse model. These results further demonstrated that LLL12 is potent in suppressing tumor growth from the breast cancer initiating cells in vivo.

Example 14

Uses of LLL12 and Related Compounds

The present invention provides options that are advantageous over previously-known compounds, compositions, formulations, research tools, diagnostics, and therapies. With regard to therapeutic superiority, because the present compounds are selective for STAT3 inhibition, the present compounds do not have the potential toxic side effects of previously-known treatment methods. In other words, there present invention provides compounds and methods with little or not impact non-cancerous cells. Moreover, the selective nature and potentency of the present compounds allow synergy with conventional anti-cancer agents, thereby reducing the overall toxic load of any given treatment. In effect, the present compounds allow conventional anti-cancer treatments to exert greater effect at lower dosage. In certain non-limiting examples, an effective dose (ED50) for an anti-cancer agent or combination of conventional anti-cancer agents when used in combination with the present compounds can be less than the ED50 for the anti-cancer agent alone. Also, in certain non-limiting embodiments, the therapeutic index (TI) for such anti-cancer agent or combination of such anti-cancer agent when used in combination with a compound herein is greater than the TI for conventional anti-cancer agent regimen alone.

In yet other embodiments, the method combines the present compounds with other therapies such as chemotherapies and/or radiation therapies, including ionizing radiation, gamma radiation, or particle beams.

Dosages and Dosage Schedules:

The dosage regimen can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

Non-limiting examples of suitable dosages can include total daily dosage of between about 25-4000 mg/m$^2$ administered orally once-daily, twice-daily or three times-daily, continuous (every day) or intermittently (e.g., 3-5 days a week). For example, the compositions can be administered in a total daily dose, or divided into multiple daily doses such as twice daily, and three times daily.

Other non-limiting examples of suitable dosages and methods of administration can include the intravenous administration directly to the tumor site via a catheter.

In addition, the administration can be continuous, i.e., every day, or intermittently. The terms "intermittent" or "intermittently" as used herein means stopping and starting at either regular or irregular intervals. For example, intermittent administration may be administration one to six days per week or it may mean administration in cycles (e.g., daily administration for two to eight consecutive weeks, then a rest period with no administration for up to one week) or it may mean administration on alternate days.

In addition, the compositions may be administered according to any of prescribed schedules, consecutively for a few weeks, followed by a rest period. For example, the composition may be administered according to any one of the prescribed schedules from two to eight weeks, followed by a rest period of one week, or twice daily at a dose for three to five days a week.

It should be apparent to a person skilled in the art that the various dosages and dosing schedules described herein merely set forth specific embodiments and should not be construed as limiting the broad scope of the invention. Any permutations, variations and combinations of the dosages and dosing schedules are included within the scope of the present invention.

Pharmaceutical Compositions:

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds described herein, and a pharmaceutically acceptable carrier. Preferably, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

The pharmaceutical compositions can be administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Non-limiting examples of solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Non-limiting examples of liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In certain embodiments, the active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For example, the compounds may be administered intravenously on the first day of treatment, with oral administration on the second day and all consecutive days thereafter. The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that, are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound or formulation administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM.

In another embodiment, the concentration of the compound in the patient's plasma is maintained at ranges between about 10 to about 50 nM. The optimal amount of the compound that should be administered to the patient in the practice of the present invention will depend on the particular compound used and the type of cancer being treated.

What is claimed is:

1. A compound having the general formula II:

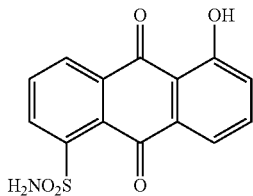

[Formula II]

and intermediates, isomers, solvates, hydrates, and salts thereof.

2. A composition of matter, comprising a compound of claim 1 and a pharmaceutically-acceptable excipient, carrier, diluents, or salt.

3. A method to synthesize a compound of claim 1, comprising:
   i. reacting an unsubstituted or substituted naphthalene sulfonyl chloride compound with a nitrogen containing compound to form an unsubstituted or substituted naphthalene sulfonyl amine;
   ii. oxidizing the unsubstituted or substituted naphthalene sulfonyl amine of step i) to yield an unsubstituted or substituted naphthoquinone compound; and
   iii. catalyzing via a Diels-Alder reaction of 3-hydroxy-2-pyrone with the unsubstituted or substituted naphthoquinone compound of step ii) to yield a compound of formula II.

4. A method of claim 3, wherein the nitrogen containing compound of step i) comprises ammonium hydroxide and the naphthalene sulfonyl chloride is unsubstituted.

5. A method to inhibit STAT3 activation in a cell, comprising introducing a compound of claim 1 to a STAT3-expressing cell, and measuring STAT3 activation inhibition.

6. A method of claim 5, wherein said inhibition is measured by observing cell apoptosis.

7. A method of claim 5, wherein said inhibition is measured by observing prevention of STAT3 SH2 dimerization.

8. A method of claim 5, wherein said inhibition is measured by observing a decrease in the levels of expression of STAT3 phosphorylation.

9. A method of claim 5, wherein said inhibition is measured by observing inhibition of downstream targets of STAT3.

10. A method of claim 9, wherein said downstream targets are selected from the group consisting of: cyclin; Bcl-2; and survivin.

11. A method of claim 5, wherein said inhibition is measured by observing induction of cleaved PARP and caspase-3.

12. A method of claim 5, wherein said inhibition is measured by inducing IL-6 in MDA-MD-453 breast cancer cells and observing a reduction in phosphorylation after induction.

13. A method of claim 5, wherein said inhibition is measured by observing reduction of STAT3 DNA binding activity after said compound introduction.

14. A method of claim 5, wherein said inhibition is measured by observing reduction of STAT3-dependent transcriptional activity after said compound introduction.

15. A method to inhibit transcription of STAT3 regulated genes, comprising administering a compound of claim 1.

16. A method of claim 15, wherein said transcription inhibition is measured via reverse transcriptase PCR.

17. A method to decrease the ability of tumor cells to form colonies, comprising administering a compound of claim 1 to a tumor cell-containing medium.

18. A method of claim 17, wherein said tumor cell-containing medium is a mammalian cell culture.

19. A method of claim 17, wherein said tumor cell-containing medium is a mammal.

20. A method of claim 19, wherein said mammal is selected from the group consisting essentially of: human; livestock; companion animal; and zoo animal.

21. A method to inhibit tumor cell migration, comprising administering a compound of claim 1 to a tumor cell-containing medium.

22. A method of claim 21, wherein said tumor cell-containing medium is a mammalian cell culture.

23. A method of claim 21, wherein said tumor cell-containing medium is a mammal.

24. A method of claim 23, wherein said mammal is selected from the group consisting essentially of: human; livestock; companion animal; and zoo animal.

25. A method to inhibit tumor cell proliferation, comprising administering a compound of claim 1 to a tumor cell-containing medium.

26. A method of claim 25, wherein said tumor cell-containing medium is a mammalian cell culture.

27. A method of claim 25, wherein said tumor cell-containing medium is a mammal.

28. A method of claim 27, wherein said mammal is selected from the group consisting essentially of: human; livestock; companion animal; and zoo animal.

29. A method to treat a cancer having constitutively active STAT3 in a patient in need of such treatment, comprising administering a therapeutically-effective pharmaceutically-acceptable formulation of at least one compound of claim 1.

30. A method of claim 29, wherein said cancer treated is selected from the group consisting of: breast cancer; glioblastoma; and pancreatic adenocarcinoma.

31. A method of claim 29, which further comprises administering to the patient at least one additional chemotherapeutic drug.

32. A method of claim 29, wherein said additional chemotherapeutic drug is doxorubicin.

33. A method of claim 29, wherein said additional chemotherapeutic drug is gemcitabine.

34. A method of claim 29, wherein said additional chemotherapeutic drugs are doxorubicin and gemcitabine.

35. A method to determine the presence of cancer cells in a sample, comprising introducing a compound of claim 1 to a cell sample, and identifying whether STAT3 activation is inhibited.

36. A method to identify compounds useful to inhibit STAT3 activation, comprising comparing the ability of a compound of claim 1 to inhibit STAT3 activation to the ability of a test compound to inhibit STAT3 activation.

37. A kit comprising a compound of claim 1.

38. A kit of claim 37, which further comprises nucleic acid molecules useful to identify STAT3 transcription.

39. A pharmaceutically-acceptable formulation useful for treating cancer, comprising a compound of claim 1 and at least one pharmaceutically-acceptable salt.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gctggagccc gtgaaaaaga                                               20

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ctccgcctct ggcattttg                                                19

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
accaggtgag aagtgaggga                                               20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
aacagtagag gagccaggga                                               20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
tctttgagtt cggtggggtc                                               20

<210> SEQ ID NO 6
<211> LENGTH: 21
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 6
tgcatatttg tttggggcag g                                              21

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
ttggacaatg gactggttga                                                20

<210> SEQ ID NO 8
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
gtagagtgga tggtcagtg                                                 19

<210> SEQ ID NO 9
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tgatgacatc aagaaggtgg tgaag                                          25

<210> SEQ ID NO 10
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tccttggagg ccatgtgggc at                                             22

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ggccctgtca ctcctgagat                                                20

<210> SEQ ID NO 12
```

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
ggcatccagg ttatcgggga                                              20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13
cgcagacatc gtcatccagt                                              20

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14
ggattggcct tggaagatga                                              20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 15
caacatccag gacaacatgg                                              20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 16
ggacttgccc aggtcatcta                                              20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 17
tgtcttgctg ctggtcattc          20

<210> SEQ ID NO 18
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
catctgggcc acgcacatt          19

<210> SEQ ID NO 19
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ggagtccgca gtcttacgag          20

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
tctggaggac ctggtagagg          20

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
tcctggttat gggcctacag          20

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ctggccctgg tggtagaata          20